United States Patent
Nakatsuru et al.

(10) Patent No.: US 8,003,098 B2
(45) Date of Patent: Aug. 23, 2011

(54) METHODS FOR DAMAGING CELLS USING EFFECTOR FUNCTIONS OF ANTI-EPHA4 ANTIBODIES

(75) Inventors: Shuichi Nakatsuru, Kanagawa (JP); Megumi Yoshikawa, Kanagawa (JP); Shinichi Hiroshima, Kanagawa (JP); Yoshiro Kishi, Aichi (JP); Motoki Kuhara, Aichi (JP); Shiyo Nishida, Aichi (JP); Midori Shinohara, Aichi (JP)

(73) Assignee: Oncotherapy Science, Inc. (JP)

(*) Notice: Subject to any disclaimer, the term of this patent is extended or adjusted under 35 U.S.C. 154(b) by 214 days.

(21) Appl. No.: 12/280,950

(22) PCT Filed: Feb. 22, 2007

(86) PCT No.: PCT/JP2007/053858
§ 371 (c)(1), (2), (4) Date: Dec. 22, 2008

(87) PCT Pub. No.: WO2007/102383
PCT Pub. Date: Sep. 13, 2007

(65) Prior Publication Data
US 2009/0191211 A1    Jul. 30, 2009

Related U.S. Application Data

(60) Provisional application No. 60/777,794, filed on Feb. 28, 2006.

(51) Int. Cl.
*A61K 39/00* (2006.01)
(52) U.S. Cl. ............... 424/133.1; 424/138.1; 424/181.1; 530/387.3; 530/387.7; 530/391.1; 530/391.7
(58) Field of Classification Search ............... 424/133.1, 424/138.1, 181.1; 530/387.3, 387.7, 391.1, 530/391.7
See application file for complete search history.

(56) References Cited

U.S. PATENT DOCUMENTS

| | | | |
|---|---|---|---|
| 2005/0260639 A1 | 11/2005 | Nakamura et al. | |
| 2006/0039904 A1 | 2/2006 | Wu et al. | |
| 2007/0253954 A1 | 11/2007 | Nakamura et al. | |
| 2010/0040641 A1 | 2/2010 | Tsunoda et al. | |

FOREIGN PATENT DOCUMENTS

| | | | |
|---|---|---|---|
| WO | WO 95/28484 A1 | 10/1995 | |
| WO | WO 03/009814 A2 | 2/2003 | |
| WO | WO 2004/031412 A2 | 4/2004 | |
| WO | WO 2005/048917 A2 | 6/2005 | |
| WO | WO 2005/083086 A2 | 9/2005 | |
| WO | WO 2006/047639 A2 | 5/2006 | |

OTHER PUBLICATIONS

Ashida, S., et al., "Molecular Features of the Transition from Prostatic Intraepithelial Neoplasia (PIN) to Prostate Cancer: Genome-wide Gene-expression Profiles of Prostate Cancers and PINs," *Cancer Research*, vol. 64(17), pp. 5963-5972 (Sep. 1, 2004).
Dottori, M., et al., "EphA4 (Sek1) receptor tyrosine kinase is required for the development of the corticospinal tract," *Proc. Natl. Acad. Sci. USA*, vol. 95(22), pp. 13248-13253 (Oct. 27, 1998).
Iiizumi, M., et al., "EphA4 receptor, overexpressed in pancreatic ductal adenocarcinoma, promotes cancer cell growth," *Cancer Sci.*, vol. 97(11), pp. 1211-1216 (Nov. 2006, Epub Sep. 5, 2006).
Irving, et al., "Progressive Spatial Restriction of *Sek-1* and *Krox-20* Gene Expression during Hindbrain Segmentation," *Developmental Biology*, vol. 173(1), pp. 26-38 (Jan. 10, 1996).
Yao, V., et al., "Targeting Pancreatic Islets with Phage Display Assisted by Laser Pressure Catapult Microdissection," *American Journal of Pathology*, vol. 166(2), pp. 625-636 (Feb. 17, 2005).
Carles-Kinch, et al.; "Antibody Targeting of the EphA2 Tyrosine Kinase Inhibits Malignant Cell Behavior;" *Cancer Research*; 62(10): 2840-2847 (May 2002).
Coffman, et al.; "Differential EphA2 Epitope Display on Normal versus Malignant Cells;" *Cancer Research*; 63(22):7907-7912 (Nov. 2003).
Dodelet, Vincent C. and Elena B. Pasquale; "Eph receptors and ephrin ligands: embryogenesis to tumorigenesis;" *Oncogene*; 20(19):5614-5619 (Nov. 2000).
Kullander, Klas and Rüdiger Klein; "Mechanisms and Functions of Eph and Ephrin Signalling;" *Nature Review: Molecular Cell Biology*; 3(7):475-486 (Jul. 2002).
Kullander, et al.; "Kinase-Dependent and Kinase-Independent Functions of EphA4 Receptors in Major Axon Tract Formation In Vivo;" *Neuron*; 29(1):73-84 (Jan. 2001).
Murai, Keith K. and Elena B. Pasquale; "'Eph'ective signaling; forward, reverse and crosstalk;" *Journal of Cell Science*; 116(Pt. 14):2823-2832 (Jul. 2003).

*Primary Examiner* — Misook Yu
*Assistant Examiner* — Brad Duffy
(74) *Attorney, Agent, or Firm* — Kilpatrick Townsend and Stockton LLP.

(57) ABSTRACT

The present invention relates to the use of cytotoxicity based on the effector function of anti-EphA4 antibodies. Specifically, the present invention provides methods and pharmaceutical compositions that comprise an anti-EphA4 antibody as an active ingredient for damaging EphA4-expressing cells using antibody effector function. Since EphA4 is strongly expressed in pancreatic cancer cells, the present invention is particularly useful in pancreatic cancer therapies.

8 Claims, 1 Drawing Sheet

SEQUENCE LISTING

<160> NUMBER OF SEQ ID NOS: 30

<210> SEQ ID NO 1
<211> LENGTH: 6364
<212> TYPE: DNA
<213> ORGANISM: Homo sapiens
<220> FEATURE:
<221> NAME/KEY: CDS
<222> LOCATION: (43)..(3003)

<400> SEQUENCE: 1
ctgggataga agcggcagga gcagcgttgg caccggcgaa cc atg gct ggg att    54
                                                Met Ala Gly Ile

```
                                                                   1
ttc tat ttc gcc cta ttt tcg tgt ctc ttc ggg att tgc gac gct gtc    102
Phe Tyr Phe Ala Leu Phe Ser Cys Leu Phe Gly Ile Cys Asp Ala Val
 5               10                  15                  20 aca ggt tcc agg gta tac ccc gcg aat gaa gtt acc tta ttg gat tcc    150
Thr Gly Ser Arg Val Tyr Pro Ala Asn Glu Val Thr Leu Leu Asp Ser
             25                  30                  35 aga tct gtt cag gga gaa ctt ggg tgg ata gca agc cct ctg gaa gga    198
Arg Ser Val Gln Gly Glu Leu Gly Trp Ile Ala Ser Pro Leu Glu Gly
         40                  45                  50 ggg tgg gag gaa gtg agt atc atg gat gaa aaa aat aca cca atc cga    246
Gly Trp Glu Glu Val Ser Ile Met Asp Glu Lys Asn Thr Pro Ile Arg
             55                  60                  65 acc tac caa gtg tgc aat gtg atg gaa ccc agc cag aat aac tgg cta    294
Thr Tyr Gln Val Cys Asn Val Met Glu Pro Ser Gln Asn Asn Trp Leu
         70                  75                  80 cga act gat tgg atc acc cga gaa ggg gct cag agg gtg tat att gag    342
Arg Thr Asp Trp Ile Thr Arg Glu Gly Ala Gln Arg Val Tyr Ile Glu
85              90                  95                 100 att aaa ttc acc ttg agg gac tgc aat agt ctt ccg ggc gtc atg ggg    390
Ile Lys Phe Thr Leu Arg Asp Cys Asn Ser Leu Pro Gly Val Met Gly
             105                 110                 115 act tgc aag gag acg ttt aac ctg tac tac tat gaa tca gac aac gac    438
Thr Cys Lys Glu Thr Phe Asn Leu Tyr Tyr Tyr Glu Ser Asp Asn Asp
         120                 125                 130 aaa gag cgt ttc atc aga gag aac cag ttt gtc aaa att gac acc att    486
Lys Glu Arg Phe Ile Arg Glu Asn Gln Phe Val Lys Ile Asp Thr Ile
             135                 140                 145 gct gct gat gag agc ttc acc caa gtg gac att ggt gac aga atc atg    534
Ala Ala Asp Glu Ser Phe Thr Gln Val Asp Ile Gly Asp Arg Ile Met
         150                 155                 160 aag ctg aac acc gag atc cgg gat gta ggg cca tta agc aaa aag ggg    582
Lys Leu Asn Thr Glu Ile Arg Asp Val Gly Pro Leu Ser Lys Lys Gly
165             170                 175                 180 ttt tac ctg gct ttt cag gat gtg ggg gcc tgc atc gcc ctg gta tca    630
Phe Tyr Leu Ala Phe Gln Asp Val Gly Ala Cys Ile Ala Leu Val Ser
             185                 190                 195 gtc cgt gtg ttc tat aaa aag tgt cca ctc aca gtc cgc aat ctg gcc    678
Val Arg Val Phe Tyr Lys Lys Cys Pro Leu Thr Val Arg Asn Leu Ala
         200                 205                 210 cag ttt cct gac acc atc aca ggg gct gat acg tct tcc ctg gtg gaa    726
Gln Phe Pro Asp Thr Ile Thr Gly Ala Asp Thr Ser Ser Leu Val Glu
             215                 220                 225 gtt cga ggc tcc tgt gtc aac aac tca gaa gag aaa gat gtg cca aaa    774
Val Arg Gly Ser Cys Val Asn Asn Ser Glu Glu Lys Asp Val Pro Lys
         230                 235                 240 atg tac tgt ggg gca gat ggt gaa tgg ctg gta ccc att ggc aac tgc    822
Met Tyr Cys Gly Ala Asp Gly Glu Trp Leu Val Pro Ile Gly Asn Cys
245             250                 255                 260 cta tgc aac gct ggg cat gag gag cgg agc gga gaa tgc caa gct tgc    870
Leu Cys Asn Ala Gly His Glu Glu Arg Ser Gly Glu Cys Gln Ala Cys
             265                 270                 275 aaa att gga tat tac aag gct ctc tcc acg gat gcc acc tgt gcc aag    918
Lys Ile Gly Tyr Tyr Lys Ala Leu Ser Thr Asp Ala Thr Cys Ala Lys
         280                 285                 290 tgc cca ccc cac agc tac tct gtc tgg gaa gga gcc acc tcg tgc acc    966
Cys Pro Pro His Ser Tyr Ser Val Trp Glu Gly Ala Thr Ser Cys Thr
             295                 300                 305 tgt gac cga ggc ttt ttc aga gct gac aac gat gct gcc tct atg ccc    1014
Cys Asp Arg Gly Phe Phe Arg Ala Asp Asn Asp Ala Ala Ser Met Pro
```

|  |  |
|---|---|
| ```
            310                 315                 320
tgc acc cgt cca cca tct gct ccc ctg aac ttg att tca aat gtc aac
Cys Thr Arg Pro Pro Ser Ala Pro Leu Asn Leu Ile Ser Asn Val Asn
325                 330                 335                 340 gag aca tct gtg aac ttg gaa tgg agt agc cct cag aat aca ggt ggc
Glu Thr Ser Val Asn Leu Glu Trp Ser Ser Pro Gln Asn Thr Gly Gly
                    345                 350                 355 cgc cag gac att tcc tat aat gtg gta tgc aag aaa tgt gga gct ggt
Arg Gln Asp Ile Ser Tyr Asn Val Val Cys Lys Lys Cys Gly Ala Gly
                360                 365                 370 gac ccc agc aag tgc cga ccc tgt gga agt ggg gtc cac tac acc cca
Asp Pro Ser Lys Cys Arg Pro Cys Gly Ser Gly Val His Tyr Thr Pro
            375                 380                 385 cag cag aat ggc ttg aag acc acc aaa gtc tcc atc act gac ctc cta
Gln Gln Asn Gly Leu Lys Thr Thr Lys Val Ser Ile Thr Asp Leu Leu
        390                 395                 400 gct cat acc aat tac acc ttt gaa atc tgg gct gtg aat gga gtg tcc
Ala His Thr Asn Tyr Thr Phe Glu Ile Trp Ala Val Asn Gly Val Ser
405                 410                 415                 420 aaa tat aac cct aac cca gac caa tca gtt tct gtc act gtg acc acc
Lys Tyr Asn Pro Asn Pro Asp Gln Ser Val Ser Val Thr Val Thr Thr
                    425                 430                 435 aac caa gca gca cca tca tcc att gct ttg gtc cag gct aaa gaa gtc
Asn Gln Ala Ala Pro Ser Ser Ile Ala Leu Val Gln Ala Lys Glu Val
                440                 445                 450 aca aga tac agt gtg gca ctg gct tgg ctg gaa cca gat cgg ccc aat
Thr Arg Tyr Ser Val Ala Leu Ala Trp Leu Glu Pro Asp Arg Pro Asn
            455                 460                 465 ggg gta atc ctg gaa tat gaa gtc aag tat tat gag aag gat cag aat
Gly Val Ile Leu Glu Tyr Glu Val Lys Tyr Tyr Glu Lys Asp Gln Asn
        470                 475                 480 gag cga agc tat cgt ata gtt cgg aca gct gcc agg aac aca gat atc
Glu Arg Ser Tyr Arg Ile Val Arg Thr Ala Ala Arg Asn Thr Asp Ile
485                 490                 495                 500 aaa ggc ctg aac cct ctc act tcc tat gtt ttc cac gtg cga gcc agg
Lys Gly Leu Asn Pro Leu Thr Ser Tyr Val Phe His Val Arg Ala Arg
                    505                 510                 515 aca gca gct ggc tat gga gac ttc agt gag ccc ttg gag gtt aca acc
Thr Ala Ala Gly Tyr Gly Asp Phe Ser Glu Pro Leu Glu Val Thr Thr
                520                 525                 530 aac aca gtg cct tcc cgg atc att gga gat ggg gct aac tcc aca gtc
Asn Thr Val Pro Ser Arg Ile Ile Gly Asp Gly Ala Asn Ser Thr Val
            535                 540                 545 ctt ctg gtc tct gtc tcg ggc agt gtg gtg ctg gtg gta att ctc att
Leu Leu Val Ser Val Ser Gly Ser Val Val Leu Val Val Ile Leu Ile
        550                 555                 560 gca gct ttt gtc atc agc cgg aga cgg agt aaa tac agt aaa gcc aaa
Ala Ala Phe Val Ile Ser Arg Arg Arg Ser Lys Tyr Ser Lys Ala Lys
565                 570                 575                 580 caa gaa gcg gat gaa gag aaa cat ttg aat caa ggt gta aga aca tat
Gln Glu Ala Asp Glu Glu Lys His Leu Asn Gln Gly Val Arg Thr Tyr
                    585                 590                 595 gtg gac ccc ttt acg tac gaa gat ccc aac caa gca gtg cga gag ttt
Val Asp Pro Phe Thr Tyr Glu Asp Pro Asn Gln Ala Val Arg Glu Phe
                600                 605                 610 gcc aaa gaa att gac gca tcc tgc att aag att gaa aaa gtt ata gga
Ala Lys Glu Ile Asp Ala Ser Cys Ile Lys Ile Glu Lys Val Ile Gly
            615                 620                 625 gtt ggt gaa ttt ggt gag gta tgc agt ggg cgt ctc aaa gtg cct ggc
Val Gly Glu Phe Gly Glu Val Cys Ser Gly Arg Leu Lys Val Pro Gly
``` | 1062<br><br>1110<br><br>1158<br><br>1206<br><br>1254<br><br>1302<br><br>1350<br><br>1398<br><br>1446<br><br>1494<br><br>1542<br><br>1590<br><br>1638<br><br>1686<br><br>1734<br><br>1782<br><br>1830<br><br>1878<br><br>1926<br><br>1974 |

```
                    630                 635                 640
aag aga gag atc tgt gtg gct atc aag act ctg aaa gct ggt tat aca    2022
Lys Arg Glu Ile Cys Val Ala Ile Lys Thr Leu Lys Ala Gly Tyr Thr
645                 650                 655                 660 gac aaa cag agg aga gac ttc ctg agt gag gcc agc atc atg gga cag    2070
Asp Lys Gln Arg Arg Asp Phe Leu Ser Glu Ala Ser Ile Met Gly Gln
                665                 670                 675 ttt gac cat ccg aac atc att cac ttg gaa ggc gtg gtc act aaa tgt    2118
Phe Asp His Pro Asn Ile Ile His Leu Glu Gly Val Val Thr Lys Cys
            680                 685                 690 aaa cca gta atg atc ata aca gag tac atg gag aat ggc tcc ttg gat    2166
Lys Pro Val Met Ile Ile Thr Glu Tyr Met Glu Asn Gly Ser Leu Asp
        695                 700                 705 gca ttc ctc agg aaa aat gat ggc aga ttt aca gtc att cag ctg gtg    2214
Ala Phe Leu Arg Lys Asn Asp Gly Arg Phe Thr Val Ile Gln Leu Val
    710                 715                 720 ggc atg ctt cgt ggc att ggg tct ggg atg aag tat tta tct gat atg    2262
Gly Met Leu Arg Gly Ile Gly Ser Gly Met Lys Tyr Leu Ser Asp Met
725                 730                 735                 740 agc tat gtg cat cgt gat ctg gcc gca cgg aac atc ctg gtg aac agc    2310
Ser Tyr Val His Arg Asp Leu Ala Ala Arg Asn Ile Leu Val Asn Ser
                745                 750                 755 aac ttg gtc tgc aaa gtg tct gat ttt ggc atg tcc cga gtg ctt gag    2358
Asn Leu Val Cys Lys Val Ser Asp Phe Gly Met Ser Arg Val Leu Glu
            760                 765                 770 gat gat ccg gaa gca gct tac acc acc agg ggt ggc aag att cct atc    2406
Asp Asp Pro Glu Ala Ala Tyr Thr Thr Arg Gly Gly Lys Ile Pro Ile
        775                 780                 785 cgg tgg act gcg cca gaa gca att gcc tat cgt aaa ttc aca tca gca    2454
Arg Trp Thr Ala Pro Glu Ala Ile Ala Tyr Arg Lys Phe Thr Ser Ala
    790                 795                 800 agt gat gta tgg agc tat gga atc gtt atg tgg gaa gtg atg tcg tac    2502
Ser Asp Val Trp Ser Tyr Gly Ile Val Met Trp Glu Val Met Ser Tyr
805                 810                 815                 820 ggg gag agg ccc tat tgg gat atg tcc aat caa gat gtg att aaa gcc    2550
Gly Glu Arg Pro Tyr Trp Asp Met Ser Asn Gln Asp Val Ile Lys Ala
                825                 830                 835 att gag gaa ggc tat cgg tta ccc cct cca atg gac tgc ccc att gcg    2598
Ile Glu Glu Gly Tyr Arg Leu Pro Pro Pro Met Asp Cys Pro Ile Ala
            840                 845                 850 ctc cac cag ctg atg cta gac tgc tgg cag aag gag agg agc gac agg    2646
Leu His Gln Leu Met Leu Asp Cys Trp Gln Lys Glu Arg Ser Asp Arg
        855                 860                 865 cct aaa ttt ggg cag att gtc aac atg ttg gac aaa ctc atc cgc aac    2694
Pro Lys Phe Gly Gln Ile Val Asn Met Leu Asp Lys Leu Ile Arg Asn
    870                 875                 880 ccc aac agc ttg aag agg aca ggg acg gag agc tcc aga cct aac act    2742
Pro Asn Ser Leu Lys Arg Thr Gly Thr Glu Ser Ser Arg Pro Asn Thr
885                 890                 895                 900 gcc ttg ttg gat cca agc tcc cct gaa ttc tct gct gtg gta tca gtg    2790
Ala Leu Leu Asp Pro Ser Ser Pro Glu Phe Ser Ala Val Val Ser Val
                905                 910                 915 ggc gat tgg ctc cag gcc att aaa atg gac cgg tat aag gat aac ttc    2838
Gly Asp Trp Leu Gln Ala Ile Lys Met Asp Arg Tyr Lys Asp Asn Phe
            920                 925                 930 aca gct gct ggt tat acc aca cta gag gct gtg gtg cac gtg aac cag    2886
Thr Ala Ala Gly Tyr Thr Thr Leu Glu Ala Val Val His Val Asn Gln
        935                 940                 945 gag gac ctg gca aga att ggt atc aca gcc atc acg cac cag aat aag    2934
Glu Asp Leu Ala Arg Ile Gly Ile Thr Ala Ile Thr His Gln Asn Lys
```

-continued

```
               950                 955                 960
att ttg agc agt gtc cag gca atg cga acc caa atg cag cag atg cac   2982
Ile Leu Ser Ser Val Gln Ala Met Arg Thr Gln Met Gln Gln Met His
965                 970                 975                 980 ggc aga atg gtt ccc gtc tga gccagtactg aataaactca aaactcttga      3033
Gly Arg Met Val Pro Val
                985 aattagttta cctcatccat gcactttaat tgaagaactg cacttttttt acttcgtctt  3093
cgccctctga aattaaagaa atgaaaaaaa aaaacaatat ctgcagcgtt gcttggtgca  3153
cagattgctg aaactgtggg gcttacagaa atgactgccg tcatttgaa tgagacctgg   3213
aacaaatcgt ttctcagaag tactttctg ttcatcacca gtctgtaaaa tacatgtacc   3273
tatagaaata gaacactgcc tctgagtttt gatgctgtat ttgctgccag acactgagct  3333
tctgagacat ccctgattct ctctccattt ggaattacaa ccattgtatt ttgtttgtgg  3393
cataaattac agtcatctgt cttcactgg aatgaagacc atgcctagga acattttta   3453
aggactcagc tgtggctttt agggcttggt tcataccatg ggggaaaaaa aagtcctagg  3513
agaaagcgac gtggctcatt agtgttgcct cttcagtgct caagccgcct ggtggattcc  3573
tatgacacag ggggcctgga agaaaggga aagtggattt aaaatatata tatacgtaac   3633
ccaagcccca taacccctaa ctggacaaat gaggtctgtt tctttgggcc tgaggctgtg  3693
ccatataaag tcttattttg ggactttaca aacttgtcct aactatcttg tggatagtgg  3753
gctgtgacaa tctggaatag agaacgttca cacttcgctc ctttaaagaa gcgaccccag  3813
atctgcaagg gagtagattc tgctatcttg gcctcacagc ccttcctgtt gattacaaag  3873
cccgtggaag aaaacagaac acaccctcct cagttccgtc taaatgtgtt tcttctgctt  3933
caattacacc agttctgggg caaagacact gatgaaacaa cacccatacc tgaaaagaat  3993
aaatgtgtga ctttcaaatc ccctttcgca gtgaaagaaa cagcaaacac ttaagattca  4053
gcatctgttc tccagttgca ctgaggaatg cactgtctcg cagcaccagc tctgcagagc  4113
ccttgcccca gactctttgc ggtttttattt atatgtattt ccatatttca ttcctgtgtg  4173
tcactgctgc attggtgtgg cagcaagtga ccaaatgcta caggtcttac tatggacacc  4233
aggtcaggtg caaccacaca aaacaaagcc agttccatga gctgcctatg atatgcattg  4293
cggaagtaac attttaccca gggtgtgcca ttgcagtgat ataaatatat ttttttctta  4353
gactaaatat gagctgacta tctcttttga tgtgtgtaca taggtgtgag tgtgtgtgta  4413
tgcgtgcctg tctgtgtgcg ggtgtgtgta tgtgcatagc ctcatgctta ggactaccca  4473
tgaatgttgt ggaatgctac acctggagag ttctggtttt ccaccagttt caagatgaag  4533
aactacatga tacagtggac ctggagacca tccccttgga aagacaaccc agagatgttc  4593
agcatcctgt atctacacgc atcctgtatc tacacgtgta ttttgtagct gtcacactaa  4653
ccttaataag aattctacag cttttggacag aggcattttc accttaatgg tgaagtaatt  4713
taaaatataa atccattcag gtgacaaccc atcatcaaaa ttacaaattt tctgattgaa  4773
ctcatctgaa tcatcagttc cttgatggag agagagaagg agatgaaatg tgtctggtaa  4833
ccccaaatgg agtacaagta gcctttgttt tcctgcataa atggacttgt tgaatgcgaa  4893
cgaatatatg caattcatat acttttggag atgaacgtag atatgtgtgt cagctttgag  4953
atggtgtgtc ctgattaat actttgtctc ccaatatcac agaaaaatac atgccagtga   5013
ctcttgaggt taaggtagtt gggatgaaat ggcctcaggc aatttcacat tccctaatta  5073
cctggaaagt tctacagtaa ttaatatgca gctaactcct gttgccctca caagagcatc  5133
```

-continued

```
agccttctag aatcggagct ccggagtgtg aagattcagt attgatatga tatgtatacc    5193
aaactccagc caacttactg ccattttca taatctgagt ggctgccttg cttatcctaa     5253
gctgtggttg cagaaaccgt ggccatttat ataagctata acatcaaatc agggaaaaat    5313
gaggaaaaaa aatagattct gaaccattta ttgttaaata agtagagaaa atcatcaata    5373
aatatttatt acattctgac agggtgtgtg gcattgtgtt ctatgccaga gtgacaaagt    5433
tgattcaccc cttttgggg accttaatat attttttaag ggatgtgcct atgcattgat     5493
gcctgaaaaa tatgtataaa gaaatgaggt tgactcttct gagcagttca tcttttccag    5553
aggtaagggt aggaggccaa cttcagggtc tgggtctgag cccgtgggca agccctggcc    5613
gagtgagctc caatgctaac tcatgtgccg atctctagag cagtgggaaa ctacccgct    5673
gcaccaaatc aagtagcttc accttgtgta tgcaggcccc aagttatttt ttagcaatct    5733
tacgagtgaa atgttctggt gggttgaaaa acgttcttat tttaaagaaa ggttgtgctc    5793
gctacactgc tggtgtgtgc attctgagac ctcttgtatt caatctgtga aggatatgtg    5853
tattaatccg tacacccgta tagcctcaat atttgtctga agacacttaa attctgaccc    5913
ataaaggaaa gttctagaag caatatttc acttatttaa cattctccaa acaacatcaa     5973
gcattgatac acactgaaga gtgcgtttat tttttgtatc actctaagta tgttggaata    6033
tgcaaggact gtggttcaaa ttagaatgta taaggcatat tataatttag ttcatactga    6093
ataagaaatt aacagaacat tgttcggttc acacgttcca aactttgagt gatttctgga    6153
gttagacata gattttctat tttgttttaa tttgtcaagg tattttctt cccttcatga     6213
actttaggta cacataactt atgtcattta tttatggtct tttataccta gtttgtaaaa    6273
ttgtaaaata gcaaactaaa tgcaaagagt ttgcatttga aaataataaa gtagttgccg    6333
tatacaaccc tgcaaaaaaa aaaaaaaaaa a                                   6364
```

<210> SEQ ID NO 2
<211> LENGTH: 986
<212> TYPE: PRT
<213> ORGANISM: Homo sapiens

<400> SEQUENCE: 2

```
Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
                20                  25                  30

Leu Leu Asp Ser Arg Ser Val Gln Gly Glu Leu Gly Trp Ile Ala Ser
            35                  40                  45

Pro Leu Glu Gly Gly Trp Glu Glu Val Ser Ile Met Asp Glu Lys Asn
        50                  55                  60

Thr Pro Ile Arg Thr Tyr Gln Val Cys Asn Val Met Glu Pro Ser Gln
65                  70                  75                  80

Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
                100                 105                 110

Gly Val Met Gly Thr Cys Lys Glu Thr Phe Asn Leu Tyr Tyr Tyr Glu
            115                 120                 125

Ser Asp Asn Asp Lys Glu Arg Phe Ile Arg Glu Asn Gln Phe Val Lys
        130                 135                 140

Ile Asp Thr Ile Ala Ala Asp Glu Ser Phe Thr Gln Val Asp Ile Gly
145                 150                 155                 160
```

```
Asp Arg Ile Met Lys Leu Asn Thr Glu Ile Arg Asp Val Gly Pro Leu
            165                 170                 175
Ser Lys Lys Gly Phe Tyr Leu Ala Phe Gln Asp Val Gly Ala Cys Ile
        180                 185                 190
Ala Leu Val Ser Val Arg Val Phe Tyr Lys Lys Cys Pro Leu Thr Val
    195                 200                 205
Arg Asn Leu Ala Gln Phe Pro Asp Thr Ile Thr Gly Ala Asp Thr Ser
210                 215                 220
Ser Leu Val Glu Val Arg Gly Ser Cys Val Asn Asn Ser Glu Glu Lys
225                 230                 235                 240
Asp Val Pro Lys Met Tyr Cys Gly Ala Asp Gly Glu Trp Leu Val Pro
            245                 250                 255
Ile Gly Asn Cys Leu Cys Asn Ala Gly His Glu Glu Arg Ser Gly Glu
        260                 265                 270
Cys Gln Ala Cys Lys Ile Gly Tyr Tyr Lys Ala Leu Ser Thr Asp Ala
    275                 280                 285
Thr Cys Ala Lys Cys Pro Pro His Ser Tyr Ser Val Trp Glu Gly Ala
290                 295                 300
Thr Ser Cys Thr Cys Asp Arg Gly Phe Phe Arg Ala Asp Asn Asp Ala
305                 310                 315                 320
Ala Ser Met Pro Cys Thr Arg Pro Pro Ser Ala Pro Leu Asn Leu Ile
            325                 330                 335
Ser Asn Val Asn Glu Thr Ser Val Asn Leu Glu Trp Ser Ser Pro Gln
        340                 345                 350
Asn Thr Gly Gly Arg Gln Asp Ile Ser Tyr Asn Val Val Cys Lys Lys
    355                 360                 365
Cys Gly Ala Gly Asp Pro Ser Lys Cys Arg Pro Cys Gly Ser Gly Val
370                 375                 380
His Tyr Thr Pro Gln Gln Asn Gly Leu Lys Thr Thr Lys Val Ser Ile
385                 390                 395                 400
Thr Asp Leu Leu Ala His Thr Asn Tyr Thr Phe Glu Ile Trp Ala Val
            405                 410                 415
Asn Gly Val Ser Lys Tyr Asn Pro Asn Pro Asp Gln Ser Val Ser Val
        420                 425                 430
Thr Val Thr Thr Asn Gln Ala Ala Pro Ser Ser Ile Ala Leu Val Gln
    435                 440                 445
Ala Lys Glu Val Thr Arg Tyr Ser Val Ala Leu Ala Trp Leu Glu Pro
450                 455                 460
Asp Arg Pro Asn Gly Val Ile Leu Glu Tyr Glu Val Lys Tyr Tyr Glu
465                 470                 475                 480
Lys Asp Gln Asn Glu Arg Ser Tyr Arg Ile Val Arg Thr Ala Ala Arg
            485                 490                 495
Asn Thr Asp Ile Lys Gly Leu Asn Pro Leu Thr Ser Tyr Val Phe His
        500                 505                 510
Val Arg Ala Arg Thr Ala Ala Gly Tyr Gly Asp Phe Ser Glu Pro Leu
    515                 520                 525
Glu Val Thr Thr Asn Thr Val Pro Ser Arg Ile Ile Gly Asp Gly Ala
530                 535                 540
Asn Ser Thr Val Leu Leu Val Ser Val Ser Gly Ser Val Val Leu Val
545                 550                 555                 560
Val Ile Leu Ile Ala Ala Phe Val Ile Ser Arg Arg Arg Ser Lys Tyr
            565                 570                 575
Ser Lys Ala Lys Gln Glu Ala Asp Glu Glu Lys His Leu Asn Gln Gly
        580                 585                 590
```

Val Arg Thr Tyr Val Asp Pro Phe Thr Tyr Glu Asp Pro Asn Gln Ala
        595                 600                 605

Val Arg Glu Phe Ala Lys Glu Ile Asp Ala Ser Cys Ile Lys Ile Glu
    610                 615                 620

Lys Val Ile Gly Val Gly Glu Phe Gly Glu Val Cys Ser Gly Arg Leu
625                 630                 635                 640

Lys Val Pro Gly Lys Arg Glu Ile Cys Val Ala Ile Lys Thr Leu Lys
                645                 650                 655

Ala Gly Tyr Thr Asp Lys Gln Arg Arg Asp Phe Leu Ser Glu Ala Ser
            660                 665                 670

Ile Met Gly Gln Phe Asp His Pro Asn Ile Ile His Leu Glu Gly Val
        675                 680                 685

Val Thr Lys Cys Lys Pro Val Met Ile Ile Thr Glu Tyr Met Glu Asn
    690                 695                 700

Gly Ser Leu Asp Ala Phe Leu Arg Lys Asn Asp Gly Arg Phe Thr Val
705                 710                 715                 720

Ile Gln Leu Val Gly Met Leu Arg Gly Ile Gly Ser Gly Met Lys Tyr
                725                 730                 735

Leu Ser Asp Met Ser Tyr Val His Arg Asp Leu Ala Ala Arg Asn Ile
            740                 745                 750

Leu Val Asn Ser Asn Leu Val Cys Lys Val Ser Asp Phe Gly Met Ser
        755                 760                 765

Arg Val Leu Glu Asp Asp Pro Glu Ala Ala Tyr Thr Thr Arg Gly Gly
    770                 775                 780

Lys Ile Pro Ile Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
                805                 810                 815

Val Met Ser Tyr Gly Glu Arg Pro Tyr Trp Asp Met Ser Asn Gln Asp
            820                 825                 830

Val Ile Lys Ala Ile Glu Glu Gly Tyr Arg Leu Pro Pro Pro Met Asp
        835                 840                 845

Cys Pro Ile Ala Leu His Gln Leu Met Leu Asp Cys Trp Gln Lys Glu
    850                 855                 860

Arg Ser Asp Arg Pro Lys Phe Gly Gln Ile Val Asn Met Leu Asp Lys
865                 870                 875                 880

Leu Ile Arg Asn Pro Asn Ser Leu Lys Arg Thr Gly Thr Glu Ser Ser
                885                 890                 895

Arg Pro Asn Thr Ala Leu Leu Asp Pro Ser Ser Pro Glu Phe Ser Ala
            900                 905                 910

Val Val Ser Val Gly Asp Trp Leu Gln Ala Ile Lys Met Asp Arg Tyr
        915                 920                 925

Lys Asp Asn Phe Thr Ala Ala Gly Tyr Thr Thr Leu Glu Ala Val Val
    930                 935                 940

His Val Asn Gln Glu Asp Leu Ala Arg Ile Gly Ile Thr Ala Ile Thr
945                 950                 955                 960

His Gln Asn Lys Ile Leu Ser Ser Val Gln Ala Met Arg Thr Gln Met
                965                 970                 975

Gln Gln Met His Gly Arg Met Val Pro Val
            980                 985

<210> SEQ ID NO 3
<211> LENGTH: 23
<212> TYPE: DNA

-continued

<213> ORGANISM: artificial
<220> FEATURE:
<223> OTHER INFORMATION: An artificially synthesized primer sequence for
      RT-PCR.

<400> SEQUENCE: 3
gaaggcgtgg tcactaaatg taa                                               23

<210> SEQ ID NO 4
<211> LENGTH: 22
<212> TYPE: DNA
<213> ORGANISM: artificial
<220> FEATURE:
<223> OTHER INFORMATION: An artificially synthesized primer sequence for
      RT-PCR.

<400> SEQUENCE: 4
tttaatttca gagggcgaag ac                                                22

<210> SEQ ID NO 5
<211> LENGTH: 20
<212> TYPE: DNA
<213> ORGANISM: artificial
<220> FEATURE:
<223> OTHER INFORMATION: An artificially synthesized primer sequence for
      RT-PCR.

<400> SEQUENCE: 5
gtcagtggtg gacctgacct                                                   20

<210> SEQ ID NO 6
<211> LENGTH: 23
<212> TYPE: DNA
<213> ORGANISM: artificial
<220> FEATURE:
<223> OTHER INFORMATION: An artificially synthesized primer sequence for
      RT-PCR.

<400> SEQUENCE: 6
ggttgagcac agggtacttt att                                               23

<210> SEQ ID NO 7
<211> LENGTH: 21
<212> TYPE: DNA
<213> ORGANISM: artificial
<220> FEATURE:
<223> OTHER INFORMATION: An artificially synthesized primer sequence for
      RT-PCR.

<400> SEQUENCE: 7
gaggtgatag cattgctttc g                                                 21

<210> SEQ ID NO 8
<211> LENGTH: 21
<212> TYPE: DNA
<213> ORGANISM: artificial
<220> FEATURE:
<223> OTHER INFORMATION: An artificially synthesized primer sequence for
      RT-PCR.

<400> SEQUENCE: 8
caagtcagtg tacaggtaag c                                                 21

<210> SEQ ID NO 9
<211> LENGTH: 452
<212> TYPE: PRT
<213> ORGANISM: Homo sapiens
<220> FEATURE:

<221> NAME/KEY: MISC_FEATURE
<223> OTHER INFORMATION: An amino acid sequence of VH of anti-EPHA4 human antibody.

<400> SEQUENCE: 9

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Val | Ser | Gly | Tyr | Thr | Leu | Thr | Glu | Leu |
| | | | 20 | | | | | 25 | | | | | 30 | | |
| Ser | Met | His | Trp | Val | Arg | Gln | Ala | Pro | Gly | Lys | Gly | Leu | Glu | Trp | Met |
| | | 35 | | | | | 40 | | | | | 45 | | | |
| Gly | Gly | Phe | Asp | Pro | Glu | Asp | Gly | Glu | Thr | Ile | Tyr | Ala | Gln | Lys | Phe |
| 50 | | | | | 55 | | | | | 60 | | | | | |
| Gln | Gly | Arg | Val | Thr | Met | Thr | Glu | Asp | Thr | Ser | Thr | Asp | Thr | Ala | Tyr |
| 65 | | | | 70 | | | | | 75 | | | | | 80 | |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Thr | Ala | Gln | Pro | Phe | His | Trp | Gly | Asp | Asp | Ala | Phe | Asp | Ile | Trp |
| | | | 100 | | | | | 105 | | | | | 110 | | |
| Gly | Gln | Gly | Thr | Met | Val | Thr | Val | Ser | Ser | Ala | Ser | Thr | Lys | Gly | Pro |
| | | 115 | | | | | 120 | | | | | 125 | | | |
| Ser | Val | Phe | Pro | Leu | Ala | Pro | Ser | Ser | Lys | Ser | Thr | Ser | Gly | Gly | Thr |
| 130 | | | | | 135 | | | | | 140 | | | | | |
| Ala | Ala | Leu | Gly | Cys | Leu | Val | Lys | Asp | Tyr | Phe | Pro | Glu | Pro | Val | Thr |
| 145 | | | | 150 | | | | | 155 | | | | | 160 | |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Gln | Thr | Tyr | Ile | Cys | Asn | Val | Asn |
| | | 195 | | | | | 200 | | | | | 205 | | | |
| His | Lys | Pro | Ser | Asn | Thr | Lys | Val | Asp | Lys | Lys | Val | Glu | Pro | Lys | Ser |
| | | 210 | | | | | 215 | | | | | 220 | | | |
| Cys | Asp | Lys | Thr | His | Thr | Cys | Pro | Pro | Cys | Pro | Ala | Pro | Glu | Leu | Leu |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| His | Glu | Asp | Pro | Glu | Val | Lys | Phe | Asn | Trp | Tyr | Val | Asp | Gly | Val | Glu |
| | | 275 | | | | | 280 | | | | | 285 | | | |
| Val | His | Asn | Ala | Lys | Thr | Lys | Pro | Arg | Glu | Glu | Gln | Tyr | Asn | Ser | Thr |
| | 290 | | | | | 295 | | | | | 300 | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Ala | Leu | Pro | Ala | Pro |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Tyr | Thr | Leu | Pro | Pro | Ser | Arg | Asp | Glu | Leu | Thr | Lys | Asn | Gln | Val |
| | | 355 | | | | | 360 | | | | | 365 | | | |
| Ser | Leu | Thr | Cys | Leu | Val | Lys | Gly | Phe | Tyr | Pro | Ser | Asp | Ile | Ala | Val |
| | 370 | | | | | 375 | | | | | 380 | | | | |
| Glu | Trp | Glu | Ser | Asn | Gly | Gln | Pro | Glu | Asn | Asn | Tyr | Lys | Thr | Thr | Pro |
| 385 | | | | | 390 | | | | | 395 | | | | | 400 |

```
Pro Val Leu Asp Ser Asp Gly Ser Phe Phe Leu Tyr Ser Lys Leu Thr
            405                 410                 415
Val Asp Lys Ser Arg Trp Gln Gln Gly Asn Val Phe Ser Cys Ser Val
        420                 425                 430
Met His Glu Ala Pro His Asn His Tyr Thr Gln Lys Ser Leu Ser Leu
        435                 440                 445
Ser Pro Gly Lys
    450

<210> SEQ ID NO 10
<211> LENGTH: 5
<212> TYPE: PRT
<213> ORGANISM: Homo sapiens
<220> FEATURE:
<221> NAME/KEY: MISC_FEATURE
<223> OTHER INFORMATION: An amino acid sequence of VH CDR1 of anti-EPHA4
      human antibody.

<400> SEQUENCE: 10

Glu Leu Ser Met His
1               5

<210> SEQ ID NO 11
<211> LENGTH: 17
<212> TYPE: PRT
<213> ORGANISM: Homo sapiens
<220> FEATURE:
<221> NAME/KEY: MISC_FEATURE
<223> OTHER INFORMATION: An amino acid sequence of VH CDR2 of anti-EPHA4
      human antibody.

<400> SEQUENCE: 11

Gly Phe Asp Pro Glu Asp Gly Glu Thr Ile Tyr Ala Gln Lys Phe Gln
1               5                   10                  15
Gly

<210> SEQ ID NO 12
<211> LENGTH: 13
<212> TYPE: PRT
<213> ORGANISM: Homo sapiens
<220> FEATURE:
<221> NAME/KEY: MISC_FEATURE
<223> OTHER INFORMATION: An amino acid sequence of VH CDR3 of anti-EPHA4
      human antibody.

<400> SEQUENCE: 12

Ala Gln Pro Phe His Trp Gly Asp Asp Ala Phe Asp Ile
1               5                   10

<210> SEQ ID NO 13
<211> LENGTH: 330
<212> TYPE: PRT
<213> ORGANISM: Homo sapiens
<220> FEATURE:
<221> NAME/KEY: MISC_FEATURE
<223> OTHER INFORMATION: An amino acid sequence of VH CH of anti-EPHA4
      human antibody.

<400> SEQUENCE: 13

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Pro His Asn His Tyr Thr
305                 310                 315                 320

Gln Lys Ser Leu Ser Leu Ser Pro Gly Lys
                325                 330

<210> SEQ ID NO 14
<211> LENGTH: 216
<212> TYPE: PRT
<213> ORGANISM: Homo sapiens
<220> FEATURE:
<221> NAME/KEY: MISC_FEATURE
<223> OTHER INFORMATION: An amino acid sequence of VL of anti-EPHA4
      human antibody.

<400> SEQUENCE: 14

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Pro Pro Gly Thr Ala Pro Lys Leu Leu
            35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln

```
                65                  70                  75                  80
Ser Glu Asp Glu Ala Asp Tyr Tyr Cys Ala Ala Trp Asp Asp Ser Leu
                    85                  90                  95

Asn Gly Pro Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 15
<211> LENGTH: 13
<212> TYPE: PRT
<213> ORGANISM: Homo sapiens
<220> FEATURE:
<221> NAME/KEY: MISC_FEATURE
<223> OTHER INFORMATION: An amino acid sequence of VL CDR1 of anti-EPHA4
      human antibody.

<400> SEQUENCE: 15

Ser Gly Ser Ser Ser Asn Ile Gly Ser Asn Thr Val Asn
1               5                   10

<210> SEQ ID NO 16
<211> LENGTH: 7
<212> TYPE: PRT
<213> ORGANISM: Homo sapiens
<220> FEATURE:
<221> NAME/KEY: MISC_FEATURE
<223> OTHER INFORMATION: An amino acid sequence of VL CDR2 of anti-EPHA4
      human antibody.

<400> SEQUENCE: 16

Ser Asn Asn Gln Arg Pro Ser
1               5

<210> SEQ ID NO 17
<211> LENGTH: 11
<212> TYPE: PRT
<213> ORGANISM: Homo sapiens
<220> FEATURE:
<221> NAME/KEY: MISC_FEATURE
<223> OTHER INFORMATION: An amino acid sequence of VL CDR3 of anti-EPHA4
      human antibody.

<400> SEQUENCE: 17

Ala Ala Trp Asp Asp Ser Leu Asn Gly Pro Val
1               5                   10

<210> SEQ ID NO 18
<211> LENGTH: 105
<212> TYPE: PRT
<213> ORGANISM: Homo sapiens
<220> FEATURE:
```

```
<221> NAME/KEY: MISC_FEATURE
<223> OTHER INFORMATION: An amino acid sequence of VL CL of anti-EPHA4
      human antibody.

<400> SEQUENCE: 18

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 19
<211> LENGTH: 450
<212> TYPE: PRT
<213> ORGANISM: Homo sapiens
<220> FEATURE:
<221> NAME/KEY: MISC_FEATURE
<223> OTHER INFORMATION: An amino acid sequence of VH of anti-EPHA4
      human antibody.

<400> SEQUENCE: 19

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Leu Arg Ser Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Pro His Asn His Tyr Thr Gln Lys Ser Leu Ser Leu Ser Pro
        435                 440                 445

Gly Lys
    450

<210> SEQ ID NO 20
<211> LENGTH: 7
<212> TYPE: PRT
<213> ORGANISM: Homo sapiens
<220> FEATURE:
<221> NAME/KEY: MISC_FEATURE
<223> OTHER INFORMATION: An amino acid sequence of VH CDR1 of anti-EPHA4
      human antibody.

<400> SEQUENCE: 20

Ser Asn Ser Ala Ala Trp Asn
1               5

<210> SEQ ID NO 21
<211> LENGTH: 18
<212> TYPE: PRT
<213> ORGANISM: Homo sapiens
<220> FEATURE:
<221> NAME/KEY: MISC_FEATURE
<223> OTHER INFORMATION: An amino acid sequence of VH CDR2 of anti-EPHA4
      human antibody.

<400> SEQUENCE: 21

Arg Thr Tyr Tyr Arg Ser Lys Trp Tyr Asn Asp Tyr Ala Val Ser Val
1               5                   10                  15

Lys Ser

<210> SEQ ID NO 22
```

-continued

```
<211> LENGTH: 8
<212> TYPE: PRT
<213> ORGANISM: Homo sapiens
<220> FEATURE:
<221> NAME/KEY: MISC_FEATURE
<223> OTHER INFORMATION: An amino acid sequence of VH CDR3 of anti-EPHA4
      human antibody.

<400> SEQUENCE: 22

Asp Ser Leu Arg Ser Phe Asp Tyr
1               5

<210> SEQ ID NO 23
<211> LENGTH: 216
<212> TYPE: PRT
<213> ORGANISM: Homo sapiens
<220> FEATURE:
<221> NAME/KEY: MISC_FEATURE
<223> OTHER INFORMATION: An amino acid sequence of VL of anti-EPHA4
      human antibody.

<400> SEQUENCE: 23

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 24
<211> LENGTH: 13
<212> TYPE: PRT
<213> ORGANISM: Homo sapiens
<220> FEATURE:
<221> NAME/KEY: MISC_FEATURE
<223> OTHER INFORMATION: An amino acid sequence of VL CDR1 of anti-EPHA4
      human antibody.

<400> SEQUENCE: 24

Ser Gly Ser Ser Ser Asn Ile Gly Asn Asn Tyr Val Ser
```

<210> SEQ ID NO 25
<211> LENGTH: 7
<212> TYPE: PRT
<213> ORGANISM: Homo sapiens
<220> FEATURE:
<221> NAME/KEY: MISC_FEATURE
<223> OTHER INFORMATION: An amino acid sequence of VL CDR2 of anti-EPHA4 human antibody.

<400> SEQUENCE: 25

```
Asp Asn Asn Lys Arg Pro Ser
1               5
```

<210> SEQ ID NO 26
<211> LENGTH: 11
<212> TYPE: PRT
<213> ORGANISM: Homo sapiens
<220> FEATURE:
<221> NAME/KEY: MISC_FEATURE
<223> OTHER INFORMATION: An amino acid sequence of VL CDR3 of anti-EPHA4 human antibody.

<400> SEQUENCE: 26

```
Gly Thr Trp Asp Ser Ser Leu Ser Ala Val Val
1               5                   10
```

<210> SEQ ID NO 27
<211> LENGTH: 122
<212> TYPE: PRT
<213> ORGANISM: Homo sapiens
<220> FEATURE:
<221> NAME/KEY: MISC_FEATURE
<223> OTHER INFORMATION: heavy chain VHDJ region

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Pro Phe His Trp Gly Asp Asp Ala Phe Asp Ile Trp
            100                 105                 110

Gly Gln Gly Thr Met Val Thr Val Ser Ser
        115                 120
```

<210> SEQ ID NO 28
<211> LENGTH: 111
<212> TYPE: PRT
<213> ORGANISM: Homo sapiens
<220> FEATURE:
<221> NAME/KEY: MISC_FEATURE
<223> OTHER INFORMATION: light chain VLJ region

<400> SEQUENCE: 28

```
Gln Ser Val Leu Thr Gln Pro Pro Ser Ala Ser Gly Thr Pro Gly Gln
1               5                   10                  15
```

```
Arg Val Thr Ile Ser Cys Ser Gly Ser Ser Asn Ile Gly Ser Asn
            20                  25                  30

Thr Val Asn Trp Tyr Gln Gln Pro Gly Thr Ala Pro Lys Leu Leu
        35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110
```

<210> SEQ ID NO 29
<211> LENGTH: 120
<212> TYPE: PRT
<213> ORGANISM: Homo sapiens
<220> FEATURE:
<221> NAME/KEY: MISC_FEATURE
<223> OTHER INFORMATION: heavy chain VHDJ region

<400> SEQUENCE: 29

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Leu Arg Ser Phe Asp Tyr Trp Gly Gln
            100                 105                 110

Gly Thr Leu Val Thr Val Ser Ser
        115                 120
```

<210> SEQ ID NO 30
<211> LENGTH: 111
<212> TYPE: PRT
<213> ORGANISM: Homo sapiens
<220> FEATURE:
<221> NAME/KEY: MISC_FEATURE
<223> OTHER INFORMATION: light chain VLJ region

<400> SEQUENCE: 30

```
Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80
```

-continued

```
Thr Gly Asp Glu Ala Asp Tyr Tyr Cys Gly Thr Trp Asp Ser Ser Leu
                85              90              95

Ser Ala Val Val Phe Gly Gly Gly Thr Lys Leu Thr Val Leu Gly
            100             105             110
```

METHODS FOR DAMAGING CELLS USING EFFECTOR FUNCTIONS OF ANTI-EPHA4 ANTIBODIES

This application is a U.S. National Stage Application of PCT/JP2007/053858, filed Feb. 22, 2007, which claims the benefit of U.S. Provisional Application Ser. No. 60/777,794, filed Feb. 28, 2006, the contents of which are hereby incorporated by reference in their entirety.

TECHNICAL FIELD

The present invention relates to methods for damaging cells using the effector function of anti-EphA4 antibodies and to compositions useful therefor.

BACKGROUND ART

Pancreatic cancer has one of the highest mortality rates of any malignancy, and the 5-year-survival rate of patients is 4%. Approximately 28,000 patients are diagnosed with pancreatic cancer each year, and nearly all patients will die of their disease (Greenlee, R. T., et al, (2001) CA Cancer J Clin, 51: 15-36). The poor prognosis of this malignancy is a result of the difficulty of early diagnosis and poor response to current therapeutic methods (Greenlee, R. T., et al. (2001) CA Cancer J Clin, 51: 15-36, Klinkenbijl, J. H., et al. (1999) Ann Surg, 230: 776-82; discussion 782-4.). In particular, there are currently no identified tumor markers that allow for reliable screening at an early, potentially curative stage of the disease.

Research aimed at elucidation of carcinogenic mechanisms has revealed a number of candidate target molecules for the development of anti-tumor agents. For example, the farnesyltransferase inhibitor (FTI) has been shown to be effective in the therapy of Ras-dependent tumors in animal models (Sun J et al., (1998) Oncogene, 16:1467-73.). This pharmaceutical agent was developed to inhibit growth signal pathways related to Ras, which is dependant on post-transcriptional farnesylation. Human clinical trials where anti-tumor agents were applied in combination with the anti-HER2 monoclonal antibody, trastuzumab, in order to antagonize the proto-oncogene HER2/neu have succeeded in improving clinical response, and improved the overall survival rate of breast cancer patients. Tyrosine kinase inhibitor STI-571 is an inhibitor which selectively deactivates bcr-abl fusion protein. This pharmaceutical agent was developed for the therapy of chronic myeloid leukemia, where the constant activation of bcr-abl tyrosine kinase plays a significant role in the transformation of white blood cells. Such pharmaceutical agents are designed to inhibit the carcinogenic activity of specific gene products (Molina M A, et al., (2000) Cancer Res, 16:4744-9). Thus, in cancer cells, gene products with promoted expression are generally potential targets for the development of novel anti-tumor agents.

Another cancer therapy strategy involves the use of antibodies which bind to cancer cells. The following are representative mechanisms of antibody-mediated cancer therapy:

Missile therapy: in this approach, a pharmaceutical agent is bound to an antibody that binds specifically to cancer cells, thereby allowing the agent to act specifically on the cancer cells. This targeted distribution allows even those agents with strong side effects to act intensively on the cancer cells. In addition to pharmaceutical agents, there are also reports of approaches where precursors of pharmaceutical agents, enzymes which metabolize the precursors to an active form, and so on are bound to the antibodies.

The use of antibodies which target functional molecules: this approach inhibits the binding between growth factors and cancer cells using, for example, antibodies that bind growth factor receptors or growth factors. Proliferation of some cancer cells is highly dependent on growth factors. For example, some cancers are known to be dependent on epithelial growth factor (EGF) or vascular endothelial growth factor (VEGF) for cell growth. For such cancers, inhibiting the binding between a growth factor and cancer cells can be expected to have a therapeutic effect.

Antibody cytotoxicity: antibodies that bind to certain kinds of antigens can achieve cytotoxicity in cancer cells. With these types of antibodies, the antibody molecule itself has a direct anti-tumor effect. Antibodies that display cytotoxicity to cancer cells are gaining attention as antibody agents expected to be highly effective against tumors.

DISCLOSURE OF THE INVENTION

The present inventors previously disclosed that EphA4 is a pancreatic cancer-related gene whose expression is up-regulated in pancreatic cancer cells. See WO2004/031412, incorporated by reference in its entirety. They further disclosed that siRNA against EphA4 suppress pancreatic cell proliferation. See WO2005/083086, incorporated by reference in its entirety. Herein, the present inventors investigated antibodies capable of inducing cytotoxicity, focusing on genes such as EphA4 that show increased expression in cancer cells. The results revealed that potent cytotoxicity can be induced in EphA4-expressing cells when those cells are contacted with anti-EphA4 antibodies, thus completing the present invention.

Specifically, the present invention relates to the following pharmaceutical compositions or methods:

[1] a pharmaceutical composition for damaging an EphA4-expressing cell, the composition containing as an active ingredient an anti-EphA4 antibody as an active ingredient, wherein the antibody possesses antibody effector function;

[2] the pharmaceutical composition of [1], wherein the EphA4-expressing cell is a pancreatic cancer cell;

[3] the pharmaceutical composition of [1], wherein the anti-EphA4 antibody is a monoclonal antibody;

[4] the pharmaceutical composition of [1], wherein the antibody effector function is either antibody-dependent cytotoxicity or complement-dependent cytotoxicity, or both;

[5] the pharmaceutical composition of [1], wherein the antibody is composed of a VH and VL chain, each VH and VL chain having CDR amino acid sequences designated CDR1, CDR2 and CDR3 separated by framework amino acid sequences, the amino acid sequence of each CDR in each VH and VL chain being selected from the group consisting of:

```
human VH CDR1: ELSMH,              (SEQ ID NO: 10)

human VH CDR2: GFDPEDGETIYAQKFQG,  (SEQ ID NO: 11)

human VH CDR3: AQPFHWGDDAFDI,      (SEQ ID NO: 12)

human VL CDR1: SGSSSNIGSNTVN,      (SEQ ID NO: 15)

human VL CDR2: SNNQRPS,            (SEQ ID NO: 16)

human VL CDR3: AAWDDSLNGPV;        (SEQ ID NO: 17)
and human VH CDR1: SNSAAWN,            (SEQ ID NO: 20)

human VH CDR2: RTYYRSKWYNDYAVSVKS, (SEQ ID NO: 21)
```

-continued

```
human VH CDR3:  DSLRSFDY,            (SEQ ID NO: 22)
human VL CDR1:  SGSSSNIGNNYVS,       (SEQ ID NO: 24)
human VL CDR2:  DNNKRPS,             (SEQ ID NO: 25)
human VL CDR3:  GTWDSSLSAVV;         (SEQ ID NO: 26)
```

[6] the composition of [5], wherein the human VH corresponds to the amino acid sequence of SEQ ID NO: 27 or 29, and human VL corresponds to the amino acid sequence of SEQ ID NO: 28 or 30;

[7] the composition of [5], wherein the antibody further includes the Fc domain of human IgG1;

[8] an antibody composed of a VH and VL chain, each VH and VL chain having CDR amino acid sequences designated CDR1, CDR2 and CDR3 separated by framework amino acid sequences, the amino acid sequence of each CDR in each VH and VL chain being selected from the group consisting of:

```
human VH CDR1:  ELSMH,               (SEQ ID NO: 10)
human VH CDR2:  GFDPEDGETIYAQKFQG,   (SEQ ID NO: 11)
human VH CDR3:  AQPFHWGDDAFDI,       (SEQ ID NO: 12)
human VL CDR1:  SGSSSNIGSNTVN,       (SEQ ID NO: 15)
human VL CDR2:  SNNQRPS,             (SEQ ID NO: 16)
human VL CDR3:  AAWDDSLNGPV;         (SEQ ID NO: 17)
and
human VH CDR1:  SNSAAWN,             (SEQ ID NO: 20)
human VH CDR2:  RTYYRSKWYNDYAVSVKS,  (SEQ ID NO: 21)
human VH CDR3:  DSLRSFDY,            (SEQ ID NO: 22)
human VL CDR1:  SGSSSNIGNNYVS,       (SEQ ID NO: 24)
human VL CDR2:  DNNKRPS,             (SEQ ID NO: 25)
human VL CDR3:  GTWDSSLSAVV;         (SEQ ID NO: 26)
```

[9] the antibody of [8], wherein the human VH corresponds to the amino acid sequence of SEQ ID NO: 27 or 29, and human VL corresponds to the amino acid sequence of SEQ ID NO: 28 or 30;

[10] the antibody of [8], wherein the antibody further includes the Fc domain of human IgG1;

[11] an isolated polynucleotide encoding the antibody of [8];

[12] a vector containing the polynucleotide of [11];

[13] an isolated host cell containing the vector of [12];

[14] a process for producing an antibody including the steps of culturing the host cell of [13] so that the polynucleotide is expressed, and recovering the antibody from the host cell culture;

[15] a pharmaceutical composition for damaging an EphA4-expressing cell, wherein the composition contains the polynucleotide of [11], or a vector containing same;

[16] a method for damaging an EphA4-expressing cell, including the steps of:
a) contacting the EphA4-expressing cell with an anti-EphA4 antibody, and
b) damaging the EphA4-expressing cell with the effector function of the antibody that has bound to the cell;

[17] an immunogenic composition for inducing an antibody that has an effector function against a EphA4-expressing cell, wherein the composition includes, as an active ingredient, EphA4, an immunologically active fragment thereof, or a DNA that can express EphA4 or its immunologically active fragment;

[18] a method for inducing an antibody that has an effector function against an EphA4-expressing cell, wherein the method includes the step of administering EphA4, an immunologically active fragment thereof, or a cell or a DNA that can express EphA4 or its immunologically active fragment; and

[19] a method for treating or preventing a pancreatic cancer in a subject comprising the step of administering to said subject a pharmaceutically effective amount of an anti-EphA4 antibody, or immunologically active fragment thereof, wherein the antibody possesses antibody effector function.

The present invention relates to pharmaceutical compositions for damaging EphA4-expressing cells using antibody effector function, wherein the compositions contain an anti-EphA4 antibody as an active ingredient. The present invention also relates to use of an anti-EphA4 antibody to produce pharmaceutical compositions for damaging EphA4-expressing cells using the anti-EphA4 antibody effector function. The pharmaceutical compositions of the present invention are composed of anti-EphA4 antibodies and pharmaceutically acceptable carriers.

The present inventors used cDNA microarrays for gene expression analysis of prostate or pancreatic cancer cells and normal cells collected from prostate and pancreatic cancer patients. A number of genes with specifically enhanced expression in pancreatic cancer cells were subsequently identified. Of these genes with altered expression in pancreatic cancer cells, one gene, the Eph receptor A4 (referred to herein as "EpbA4") gene encoding cytoplasmic membrane protein with low levels of expression in major organs, was selected as a candidate target gene for pancreatic cancer therapies (Nakamura T, et al. (2004) Oncogene. 2004 Mar. 25; 23(13):2385-400). By selecting genes with low levels of expression in major organs, it was presumed that the danger of side effects could be avoided. Among the proteins encoded by the genes selected in this way, anti-EphA4 antibodies were confirmed to have effector functions against EphA4-expressing cells.

The findings obtained by the present inventors show that, in a forced expression system, EphA4 tagged with c-myc-His was localized in the cytoplasmic membrane, which was confirmed using immunofluorescence microscopy. The EphA4 gene encodes an amino acid sequence expected to function as a signal peptide at its N-terminal. As mentioned above, this protein was observed to be chiefly localized in the cytoplasmic membrane, and thus it was presumed to be a transmembrane protein. In addition, the low expression level of this gene in major organs, and its high expression in pancreatic cancer cells, established EphA4 as a useful as a clinical marker and therapeutic target.

Conditions required for destroying cancer cells using effector function are, for example, the following:
Expression of large numbers of antigenic molecules on the membrane surface of cancer cells,
Uniform distribution of antigens within cancerous tissues,
Lingering of antigens bound to antibodies on the cell surface for a long time.

More specifically, for example, antigens recognized by antibodies must be expressed on the surface of the cell membrane. In addition, it is preferable that the ratio of antigen-positive cells is as high as possible in cells forming the cancerous tissues. In an ideal situation, all cancer cells are antigen-positive. When antigen-positive and negative cells are mixed in cancer cell populations, the clinical therapeutic effect of an antibody specific thereto will be substantially diminished.

Generally, when the maximum possible number of molecules is expressed on the cell surface, potent effector functions can be expected. It is also important that an antibody bound to such an antigen not be taken up into cells. Some receptors are taken up into cells (endocytosis) after binding to a ligand. Equally, antibodies bound to cell surface antigens can also be taken up into the cell. This kind of phenomenon, whereby antibodies are taken up into cells, is called internalization. When internalization occurs, the antibody constant (Fc) region is taken up into the cell. However, cells or molecules essential to effector function remain outside the antigen-expressing cells. Thus, internalization inhibits antibody effector function. Therefore, when antibody effector function is desired, it is important to select an antigen that results in limited antibody internalization. The present inventors revealed for the first time that EphA4 is a target antigen possessing such a property.

The words "a", "an", and "the" as used herein mean "at least one" unless otherwise specifically indicated.

An "isolated" or "purified" polypeptide is a polypeptide that is substantially free of cellular material, such as carbohydrate, lipid, or other contaminating proteins from the cell or tissue source from which the protein is derived, and/or substantially free of chemical precursors or other chemicals when chemically synthesized. The term "substantially free of cellular material" encompasses preparations of a polypeptide in which the polypeptide is separated from cellular components of the cells from which it is isolated or recombinantly produced. Thus, a polypeptide that is substantially free of cellular material includes preparations of polypeptide having less than about 30%, 20%, 10%, or 5% (by dry weight) of heterologous protein (also referred to herein as a "contaminating protein"). When the polypeptide is recombinantly produced, it is also preferably substantially free of culture medium, which includes preparations of polypeptide with culture medium less than about 20%, 10%, or 5% of the volume of the protein preparation. When the polypeptide is produced by chemical synthesis, it is preferably substantially free of chemical precursors or other chemicals, which includes preparations of polypeptide with chemical precursors or other chemicals involved in the synthesis of the protein less than about 30%, 20%, 10%, 5% (by dry weight) of the volume of the protein preparation. That a particular protein preparation contains an isolated or purified polypeptide can be shown, for example, by the appearance of a single band following sodium dodecyl sulfate (SDS)-polyacrylamide gel electrophoresis of the protein preparation and Coomassie Brilliant Blue staining of the gel. In a preferred embodiment, antibodies of the present invention or fragments thereof are isolated or purified.

An "isolated" or "purified" nucleic acid molecule is one which is separated from other nucleic acid molecules which are present in the natural source of the nucleic acid molecule. An "isolated" or "purified" nucleic acid molecule, for example a cDNA molecule, can be substantially free of other cellular material, or culture medium when produced by recombinant techniques, or substantially free of chemical precursors or other chemicals when chemically synthesized. In a preferred embodiment, nucleic acid molecules encoding antibodies of the present invention or fragments thereof are isolated or purified.

"Antibodies" and "immunoglobulins" are glycoproteins having the same structural characteristics. While antibodies exhibit binding specificity to a specific antigen, immunoglobulins include both antibodies and other antibody-like molecules, for which antigen specificity has not been defined. Polypeptides of the latter kind are, for example, produced at low levels by the lymph system and at increased levels by myelomas.

"Native antibodies and immunoglobulins" are typically heterotetrameric glycoproteins of about 150,000 daltons, composed of two identical light (L) chains and two identical heavy (H) chains. Each light chain is linked to a heavy chain by one covalent disulfide bond, while the number of disulfide linkages between the heavy chains of different immunoglobulin isotypes may vary. Each heavy and light chain also has regularly spaced intrachain disulfide bridges. Each heavy chain has at one end a variable domain (VH) followed by a number of constant domains (CH). Each light chain has a variable domain at one end (VL) and a constant domain at its other end (CL); the constant domain of the light chain is aligned with the first constant domain of the heavy chain, and the light chain variable domain is aligned with the variable domain of the heavy chain. Certain amino acid residues are believed to form an interface between the light- and heavy-chain variable domains (Chothia et al., (1985) J Mol Biol.; 186:651-63; Novotny and Haber, (1985) Proc Natl Acad Sci USA.; 82:4592-6).

The term "variable" refers to the fact that certain portions of the variable domains differ extensively in sequence among antibodies and are therefore presumed to be involved in the binding and specificity of each particular antibody for its particular antigen. However, the variability is not evenly distributed throughout the variable domains of antibodies. Rather, it is generally concentrated in three segments called "complementarity-determining regions" (also known as "CDRs") or hypervariable regions both in the light-chain and the heavy-chain variable domains. The more highly conserved portions of variable domains are called the framework (FR). The variable domains of native heavy and light chains each include four framework regions, largely adopting a β-sheet configuration, connected by three CDRs, which form loops connecting, and in some cases forming part of the β-sheet structure. The CDRs in each chain are held together in close proximity by the framework regions and, with the CDRs from the other chain, contribute to the formation of the three dimensional antigen-binding site of an antibody (Kabat et al., (1991) Sequences of Proteins of Immunological Interest, Fifth Edition, National Institute of Health, Bethesda, Md.). The constant domains are not directly involved in binding an antibody to an antigen but exhibit various effector functions, for example participation of the antibody in antibody-dependent cellular toxicity.

Papain digestion of an antibody yields two identical antigen-binding fragments, called "Fab" fragments, each with a single antigen-binding site, and a residual "Fc" fragment. Pepsin treatment yields an $F(ab')_2$ fragment that has two antigen-binding sites. "Fv" is the minimum antibody fragment which contains a complete antigen-recognition and -binding site. This region is generally composed of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv composed of only three CDRs specific for an antigen) has the ability to recognize and bind antigen, although at a lower affinity than the entire binding site.

The Fab fragment also contains the constant domain of the light chain and the first constant domain (CH-1) of the heavy chain. Fab' fragments differ from Fab fragments by the addition of a few residues at the carboxy terminus of the heavy chain CH-1 domain including one or more cysteines from the antibody hinge region. Fab'-SH is the designation herein for Fab', in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known in the art.

The "light chains" of antibodies (immunoglobulins) from any vertebrate species can be assigned to one of two clearly distinct types, referred to as κ (kappa) and λ (lambda), respectively, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains that correspond to the different classes of immunoglobulins are called α, δ, ε, γ, and μ, respectively. The subunit structures and three-dimensional configurations of different classes of immunoglobulins are well known in the art.

The term "monoclonal antibody" as used herein refers to an antibody obtained from a population of substantially homogeneous antibodies, i.e., the individual antibodies within the population are identical, with the exception of possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In addition to their specificity, the monoclonal antibodies are advantageous in that they can be synthesized by hybridoma culture, uncontaminated by other immunoglobulins. Thus, the modifier "monoclonal" indicates the character of the antibody as being obtained from a substantially homogeneous population of antibodies, and is not to be construed as requiring production of the antibody by any particular method. For example, the monoclonal antibodies of the present invention can be made by the hybridoma method first described by Kohler and Milstein, (1975) Nature.; 256:495-7, or can be made by recombinant DNA methods (Cabilly et al., (1984) Proc Natl Acad Sci USA.; 81:3273-7).

The monoclonal antibodies described herein specifically include "chimeric" antibodies or immunoglobulins, in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., (1984) Proc Natl Acad Sci USA.; 81:6851-5). The most common chimeric antibodies or immunoglobulins are composed of human and murine antibody fragments, generally human constant and mouse variable regions.

"Humanized" forms of non-human (e.g., murine) antibodies are specific chimeric immunoglobulins, immunoglobulin chains or fragments thereof which contain minimal sequence derived from non-human immunoglobulin. Such fragments also include Fv, Fab, Fab', F(ab')$_2$, and other antigen-binding subsequences of antibodies. For the most part, humanized antibodies are human immunoglobulins (recipient antibody) in which residues from a complementarity-determining region (CDR) of the recipient are replaced by residues derived from a CDR of a non-human species (donor antibody), for example a mouse, rat, or rabbit having the desired specificity, affinity, and capacity. In some instances, Fv framework residues of the human immunoglobulin may be replaced by corresponding non-human residues. In the context of the present invention, only a few, two, or preferably one, of framework(s) in the humanized antibody are replaced by that of non-human residues. Furthermore, humanized antibodies can contain residues which are found neither in the recipient antibody nor in the imported CDR or framework sequences. These modifications are generally introduced to further refine and optimize antibody performance. In general, a humanized antibody will include substantially all of at least one, and typically two, variable domains, in which all or substantially all of the CDR regions correspond to those of a non-human immunoglobulin and all or substantially all of the framework regions are those of a human immunoglobulin consensus sequence. A humanized antibody optimally also will include at least a portion of an immunoglobulin constant region (Fc), typically that of a human immunoglobulin. For further details see Jones et al., (1986) Nature.; 321:522-5; Riechmann et al., (1988) Nature.; 332:323-7; Presta, (1992) Curr Opin Struct Biol. 2:593-6.

"Single-chain Fv" or "sFv" antibody fragments are composed of the VH and VL domains of an antibody, wherein these domains are present in a single polypeptide chain. Preferably, the Fv polypeptide further includes a polypeptide linker between the VH and VL domains which enables the sFv to form the desired three dimensional structure required for antigen binding. A number of methods have been described to discern chemical structures for converting the naturally aggregated but chemically separated light and heavy polypeptide chains from an antibody V region into an sFv molecule which will fold into a three dimensional structure substantially similar to the structure of an antigen-binding site (U.S. Pat. Nos. 5,091,513, 5,132,405, and 4,946,778; Pluckthun in The Pharmacology of Monoclonal Antibodies, vol. 113, Rosenberg and Moore eds., Springer-Verlag, New York, pp. 269-315 (1994)).

The Fc region (Fragment, crystallizable) mentioned above is derived from the stem of the "Y" of the antibody and is composed of two heavy chains that each contribute two to three constant domains (depending on the class of the antibody). Fc binds to various cell receptors and complement proteins. In this way, it mediates different physiological effects of antibodies (opsonization, cell lysis, degranulation of mast cells, basophils and eosinophils and other processes).

Some cells (for example, Mast cells and phagocytes) have specific receptors on their cell surface for binding antibodies. These are called Fc receptors, and, as the name suggests, these receptors interact with the Fc region of some antibodies (e.g. IgA, IgG, IgE). The engagement of a particular antibody with the Fc receptor on a particular cell will trigger the effector function of that cell (for example, phagocytes will phagocytose, mast cells will degranulate) that will ultimately result in destruction of the invading microbe. The Fc receptors are isotype-specific, which gives a great flexibility to the immune system, because different situations require only certain immune mechanisms to respond to antigens. Accordingly, in the context of the present invention, the term "effector function" refers to cytotoxicity involved with the Fc regions of antibodies. Alternatively, effector function can also be explained as a role that determines the biological activity triggered by antigen recognition of an antibody. For example, functions that drive the effect whereby the Fc regions of antibodies bound to antigens damage cells expressing those antigens, can also be referred to as antibody effector function. Herein, preferred target cells are cancer cells.

Frequently the binding of an antibody to an antigen has no direct biological effect. Rather, the significant biological effects are a consequence of the secondary "effector functions" of antibodies. The immunoglobulins mediate a variety of these effector functions. Usually the ability to carry out a particular effector function requires that the antibody bind to its antigen. However, not every immunoglobulin will mediate all effector functions. Examples of known antibody effector functions include: Antibody Dependent Cell-mediated Cytotoxicity (ADCC), Complement Dependent Cytotoxicity (CDC), and neutralizing activity. Each function is described below.

Antibody Dependent Cell-mediated Cytotoxicity (ADCC):

Effector cell functions carried out by the Fc regions of various antibodies rely heavily on antibody class. Cells exist which contain Fc receptors specific to the Fc region of immunoglobulin classes IgG, IgE, or IgA. The Fc region of IgG, IgE, and IgA class antibodies each binds to a specific Fc receptor, and cells that express a corresponding Fc receptor recognize and bind to antibodies bound to cell membranes or so on. As a result, for example, cells that have Fc receptors are activated, and function in intercellular antibody transport.

For example, an IgG class antibody is recognized by Fc receptors on T cells, NK cells, neutrophils, and macrophages. These cells bind to and are activated by the Fc region of IgG class antibodies, and express cytotoxicity against cells to which these antibodies have bound. Cells, such as T cells, NK cells, neutrophils, macrophages, which acquire cytotoxicity via antibody effector function, are called effector cells. In particular, IgG class antibodies activate effector cells via Fc receptors on these cells, and then kill target cells to which the variable regions of the antibodies are bound. This is called antibody-dependent cell-mediated cytotoxicity (ADCC). ADCC may be divided based on the type of effector cell, as follows:

ADMC: IgG-dependent macrophage-mediated cytotoxicity, and

ADCC: IgG-dependent NK-cell-mediated cytotoxicity.

There is no limitation on types of effector cells in the ADCC of the present invention. In other words, the ADCC of the present invention also encompasses ADMC, wherein macrophages are the effector cells.

Antibody ADCC is known to be an important mechanism in the conference of anti-tumor effects, particularly in cancer therapies that use antibodies (Clynes R A, et al., (2000) Nature Med., 6: 443-6.). For example, a close relationship between the therapeutic effect of anti-CD20 antibody chimeric antibodies and ADCC has been reported (Cartron G, et al., (2002) Blood, 99: 754-8.). Thus, in the context present invention, ADCC is also particularly important among antibody effector functions.

ADCC is a key effector function for the clinical efficacy of monoclonal antibodies, particularly in the area of cancer therapy. For example, ADCC is thought to be an important mechanism in the anti-tumor effects of Rituxan, Herceptin, and on the like, for which clinical application has already begun. Rituxan and Herceptin are known therapeutic agents for the treatment of non-Hodgkin's lymphoma and metastatic breast cancer, respectively.

At present, the mechanism for ADCC-mediated cytotoxicity is roughly explained as follows: effector cells, which are bridged to target cells via antibodies bound to the cell surface, are thought to induce target cell apoptosis by transmitting some sort of lethal signal to the target cells. More specifically, ADCC is mediated primarily through a set of closely related Fcγ receptors with both activating and inhibitory activities. In any case, antibodies that induce cytotoxicity by effector cells are included in the antibodies that possess effector function in the context of present invention.

To assess the ADCC activity of a molecule of interest, an in vitro ADCC assay, such as that described in U.S. Pat. No. 5,500,362 or 5,821,337 may be performed. Alternatively, or additionally, the ADCC activity of a molecule of interest may be assessed in vivo, e.g., in a animal model such as that disclosed in Clynes et al., (1998) Proc Natl Acad Sci USA.; 95:652-56.

Complement Dependent Cytotoxicity (CDC):

The Fc regions of immunoglobulins bound to antigens are known to activate complementary pathways. It has also been revealed that the activation pathway may differ depending on the class of immunoglobulin. For example, of the human antibodies, IgM and IgG activate the classical pathway. On the other hand, IgA, IgD, and IgE do not activate this pathway. Namely, the function of activating complement is limited to IgM and IgG class antibodies. Particularly, the function of lysing cells to which antibody variable regions are bound is called complement-dependent cytotoxicity (CDC).

The activated complements produce, via a number of reactions, a C5b-9 membrane attack complex (MAC) having cell membrane-damaging activity. MACs generated in this way are thought to damage viral particles and cell membranes, independently of effector cells. The mechanism for MAC-mediated cytotoxicity is based on the following. MACs possess a strong binding affinity for cell membranes. MACs bound to a cell membrane open a hole in the cell membrane, making it easy for water to flow in and out of the cell. As a result, the cell membrane is destabilized, or the osmotic pressure is changed, and the cell is destroyed. Cytotoxicity due to an activated complement only extends to membrane close to the antibody which has bound the antigen. For this reason, MAC-mediated cytotoxicity is dependent on antibody specificity. ADCC and CDC can express cytotoxicity independent of each other. However, in practice, these cytotoxicities may function in composite in living bodies.

To assess CDC activity of a molecule of interest, a CDC assay, e.g., as described in Gazzano-Santoro et al., (1997) J Immunol Methods.; 202:163-71, may be performed.

Neutralizing Activity:

Antibodies capable of depriving infectivity of pathogens and activity of toxins are known in the art. Antibody-mediated neutralization can be achieved through the binding of an antigenic variable region to an antigen, or, alternatively, can require complement mediation. For example, in some cases, anti-viral antibodies require complement mediation in order to deprive a virus of its infectivity. Fc regions are essential to the participation of complements. Thus, such antibodies possess effector function that requires Fc for neutralizing viruses and cells.

Of these, preferable effector functions herein are either ADCC or CDC, or both. The present invention is based on the finding that certain anti-EphA4 antibodies bind to EphA4-expressing cells, and then express effector function.

The present invention also relates to methods for damaging EphA4-expressing cells, such methods including the following steps:

1) contacting the EphA4-expressing cells with anti-EphA4 antibodies, and 2) damaging the EphA4-expressing cells using the effector function of the antibodies which have bound to the cells.

In the methods or pharmaceutical compositions of the present invention, any EphA4-expressing cell can be damaged or killed. For example, pancreatic cancer cells are preferable as the EphA4-expressing cells of the present invention. Of these, pancreatic carcinoma cells are preferable.

Cells and antibodies can be contacted in vivo or in vitro. When targeting in vivo cancer cells as the EphA4-expressing cells, the methods of the present invention are in fact therapeutic methods or preventative methods for cancers. Specifically, the present invention provides therapeutic methods for cancers which include the following steps:

1) administering to a cancer patient an antibody that binds EphA4, and 2) damaging cancer cells using the effector function of the antibody bound to those cells.

The present inventors confirmed that antibodies binding EphA4 effectively damage EphA4-expressing cells, in particular, pancreatic cancer cells by means of effector function. The present inventors also confirmed that EphA4 is highly expressed in pancreatic cancer cells, with a high probability. In addition, EphA4 expression levels in normal tissues are low. Taken together, this information suggests that methods of pancreatic cancer therapy wherein anti-EphA4 antibody is administered can be effective, with little danger of side effects.

Antibodies including the Fc region of IgA, IgE, or IgG are essential for expressing ADCC. Equally, the antibody Fc region of IgM or IgG is preferable for expressing CDC.

However, the antibodies of the present invention are not limited so long as they possess the desired effector function. Variants, analogs or derivatives of the Fc portion may be constructed by, for example, making various substitutions of residues or sequences. In particular, the present invention contemplates antibodies composed of Fc variants engineered with optimized Fcγ receptor affinity and specificity to thereby enhance the resulting effector function.

Variant (or analog) polypeptides include insertion variants, wherein one or more amino acid residues supplement an Fc amino acid sequence. Insertions may be located at either or both termini of the protein, or may be positioned within internal regions of the Fc amino acid sequence. Insertional variants with additional residues at either or both termini can include, for example, fusion proteins and proteins including amino acid tags or labels. For example, the Fc molecule may optionally contain an N-terminal Met, especially when the molecule is expressed recombinantly in a bacterial cell such as E. coli.

In Fc deletion variants, one or more amino acid residues in an Fc polypeptide are removed. Deletions can be effected at one or both termini of the Fc polypeptide, or with removal of one or more residues within the Fc amino acid sequence. Deletion variants, therefore, include all fragments of an Fc polypeptide sequence.

In the context of Fc substitution variants, one or more amino acid residues of an Fc polypeptide are removed and replaced with alternative residues. One of skill in the art will recognize that individual additions, deletions, insertions, or substitutions to an amino acid sequence which alters a single amino acid or a small percentage of amino acids results in the conservation of the properties of the original amino acid side-chain. They are referred to as "conservative substitutions" or "conservative modifications", wherein the alteration of a protein results in a protein with similar functions. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

In one aspect, the substitutions are conservative in nature. However the present invention is not restricted thereto and also embraces substitutions that are non-conservative, so long as the polypeptide retains the requisite antibody effector function.

Preferably, the parent polypeptide Fc region is a human Fc region, e.g., a native sequence human Fc region human IgG1 (A and non-A allotypes) or human IgG3 Fc region.

In one embodiment, the variant with improved ADCC mediates ADCC substantially more effectively than an antibody with a native sequence IgG1 or IgG3 Fc region and the antigen-binding region of the variant. Preferably, the variant includes, or consists essentially of, substitutions of two or three of the residues at positions 298, 333 and 334 of the Fc region. The numbering of the residues in an immunoglobulin heavy chain is that of the EU index as in Kabat et al., (supra), expressly incorporated herein by reference. More preferably, residues at positions 298, 333 and 334 are substituted, (e.g., with alanine residues). Moreover, in order to generate an Fc region variant having improved ADCC activity, one will generally engineer an Fc region variant with improved binding affinity for FcγRIII, which is thought to be an important FcR for mediating ADCC. For example, one may introduce an amino acid modification (e.g., an insertion, a deletion, or a substitution) into the parent Fc region at any one or more of amino acid positions 256, 290, 298, 312, 326, 330, 333, 334, 360, 378 or 430 to generate such a variant. The variant with improved binding affinity for FcγRIII may further have reduced binding affinity for FcγRII, especially reduced affinity for the inhibiting FcγRIIb receptor.

To retain the requisite antibody effector function, it is preferable to modify (add, delete, insert, or substitute) only a small number or a small percentage of amino acids. Nevertheless, numerous variant amino acid insertions, deletions and/or substitutions (e.g., from 1-50 amino acids, preferably, from 1-25 amino acids, more preferably, from 1-10 amino acids) are contemplated and are within the scope of the present invention. Alternatively, the percentage of amino acids modified is preferably 20% or less, more preferably 15% of less, more preferably 10%, even more preferably 1 to 5%. Conservative amino acid substitutions will generally be preferred, though the present invention is not limited thereto. Furthermore, alterations may be in the form of altered amino acids, such as peptidomimetics or D-amino acids.

Alternatively, in the present invention, ADCC activity may be enhanced by modifying the biochemical properties other than amino acid sequence, such as glyco chain added to Fc region. For example, it was reported that the absence of fucose residue of IgG may enhances ADCC activity (Shinkawa et al., (2003) J. Biol. Chem.: 278(5): 3466-73.). Therefore, an antibody lacking the fucose residue of the Fc region is preferred in the context of the present invention. More specifically, in order to enhance the ADCC activity, a fucose residue attached to a CH2 domain of the Fc region may be removed. Cells other than CHO may be used as host cell for expression of an antibody lacking the fucose residue of the Fc region. Herein, a fucose residue was added to an antibody by alpha-1,6-fucosyltransferase (FUT8), which is highly expressed in CHO.

Therefore, human-derived antibodies belonging to these classes are preferable in the present invention. Human antibodies can be acquired using antibody-producing cells harvested from humans, or chimeric animals transplanted with human antibody genes (Ishida I, et al., (2002) Cloning and Stem Cells., 4: 91-102.).

Furthermore, antibody Fc regions can link with arbitrary variable regions. Specifically, chimeric antibodies wherein the variable regions of different animal species are bound to human constant regions are known in the art. Alternatively, a human-human chimeric antibody can also be acquired by binding human-derived variable regions to arbitrary constant regions. In addition, CDR graft technology, where complementarity determining regions (CDRs) corresponding to human antibody variable regions are replaced with CDRs of heterologous antibodies, is also known ("Immunoglobulin genes", Academic Press (London), pp 260-274, 1989; Roguska M A, et al., (1994) Proc. Natl. Acad. Sci. USA., 91: 969-73.). By replacing CDRs, antibody binding specificity is replaced. That is, human EphA4 will be recognized by humanized antibodies in which the CDR of human EphA4-binding antibodies has been transferred. The transferred antibodies can also be called humanized antibodies. Antibodies thus-obtained and equipped with an Fc region essential to effector function can be used as the antibodies of the present invention, regardless of the origin of their variable regions. For example, antibodies including a human IgG Fc are preferable in the present invention, even if their variable regions include an amino acid sequence derived from an immunoglobulin of another class or another species.

VH and VL domains of antibodies of the present invention each include three CDRs designated as CDR1, CDR2, and CDR3, separated by framework regions. Amino acid sequences of the CDRs are not particularly limited so long as the antibody can specifically bind to EphA4. Examples of preferred CDR amino acid sequences include, but are not limited to:

```
human VH CDR1: ELSMH,            (SEQ ID NO: 10)
human VH CDR2: GFDPEDGETIYAQKFQG, (SEQ ID NO: 11)
human VH CDR3: AQPFHWGDDAFDI,    (SEQ ID NO: 12)
human VL CDR1: SGSSSNIGSNTVN,    (SEQ ID NO: 15)
human VL CDR2: SNNQRPS,          (SEQ ID NO: 16)
human VL CDR3: AAWDDSLNGPV;      (SEQ ID NO: 17)
and
human VH CDR1: SNSAAWN,          (SEQ ID NO: 20)
human VH CDR2: RTYYRSKWYNDYAVSVKS, (SEQ ID NO: 21)
human VH CDR3: DSLRSFDY,         (SEQ ID NO: 22)
human VL CDR1: SGSSSNIGNNYVS,    (SEQ ID NO: 24)
human VL CDR2: DNNKRPS,          (SEQ ID NO: 25)
human VL CDR3: GTWDSSLSAVV.      (SEQ ID NO: 26)
```

In a more preferred embodiment, VH corresponds to the amino acid sequence of SEQ ID NO: 27 or 29, and VL corresponds to the amino acid sequence of SEQ ID NO: 28 or 30.

As noted above, antibodies of the present invention may be monoclonal antibodies or polyclonal antibodies. Even when administering to humans, human polyclonal antibodies can be derived using the above-mentioned animals transferred with a human antibody gene. Alternatively, immunoglobulins which have been constructed using genetic engineering techniques, such as humanized antibodies, human-non-human chimeric antibodies, and human-human chimeric antibodies, can be used. Furthermore, methods for obtaining human monoclonal antibodies by cloning human antibody-producing cells are also known.

EphA4, or a fragment including its partial peptide, can be used as immunogens to obtain the antibodies of the present invention. The EphA4 of the present invention can be derived from any species, preferably from a mammal, for example a human, mouse, or rat, more preferably a human. The human EphA4 nucleotide sequence and amino acid sequence are known in the art. To that end, the cDNA nucleotide sequence of EphA4 (GenBank Accession No. NM_004438) is described in SEQ ID NO: 1 and the amino acid sequences coded by that nucleotide sequence is described in SEQ ID NO: 2 (GenBank Accession No. NP_004429). One skilled in the art can routinely isolate genes containing the provided nucleotide sequence, preparing a fragment of the sequence as required, and obtain a protein corresponding to the target amino acid sequence.

For example, the gene coding the EphA4 protein or its fragment can be inserted into a known expression vector, and used to transform host cells. The desired protein, or its fragment, can be collected from inside or outside host cells using arbitrary and standard methods, and can also be used as an antigen. In addition, proteins, their lysates, and chemically-synthesized proteins can be used as antigens. Furthermore, cells expressing the EphA4 protein or a fragment thereof can themselves be used as immunogens.

When using a peptide fragment as the EphA4 immunogen, it is particularly preferable to select an amino acid sequence which includes a region predicted to be an extra-cellular domain. A signal peptide is presumed to be present on the N-terminal of EphA4, extending from positions 1 to 19. Thus, for example, a region other than the N-terminal signal peptide (i.e., the initial 19 amino acid residues) is preferred as the immunogen for obtaining the antibodies of the present invention. That is to say, antibodies that bind to EphA4 extra-cellular domains are preferred as the antibodies of the present invention.

Therefore, preferable antibodies in the present invention are antibodies equipped with an Fc essential to effector function, and a variable region that can bind to an extracellular EphA4 domain. When aiming for administration to humans, it is preferable to be equipped with an IgG Fc.

Any mammal can be immunized with such an antigen. However, it is preferable to consider compatibility with parent cells used in cell fusion. Generally, rodents, lagomorphs, or primates are preferred.

Rodents include, for example, mice, rats, and hamsters. Lagomorphs include, for example, rabbits. Primates include, for example, catarrhine (old world) monkeys such as *Macaca fascicularis, Macaca mulatta*, Sacred baboons, and chimpanzees.

Methods for immunizing animals with antigens are well known in the field. Intraperitoneal or subcutaneous antigen injections are standard methods for immunizing mammals. Specifically, antigens can be diluted and suspended in an appropriate amount of phosphate buffered saline (PBS), physiological saline, or so on. As desired, antigen suspensions can be mixed with an appropriate amount of a standard adjuvant such as Freund's complete adjuvant, and administered to mammals after emulsification. Subsequently, it is preferable that antigens mixed with an appropriate amount of Freund's incomplete adjuvant are administered in multiple doses every four to 21 days. An appropriate carrier can also be used for immunization. After carrying out immunization as outlined above, standard methods can be used to examine serum for an increase in the desired antibody level.

Polyclonal antibodies against the EphA4 protein can be prepared from immunized mammals whose serum has been investigated for an increase in the desired antibodies. This can be achieved by collecting blood from these animals, or by using an arbitrary, usual method to isolate serum from their blood. In the context of the present invention, polyclonal antibodies include serum that contains polyclonal antibodies, and fractions that contain polyclonal antibodies isolated from serum. IgG and IgM can be prepared from fractions that recognize EphA4 protein by using, for example, an affinity column coupled to EphA4 protein, and then further purifying this fraction using protein A or protein G columns. In the present invention, antiserum can be used as is as polyclonal antibodies. Alternatively, purified IgG, IgM, or such can also be used.

To prepare monoclonal antibodies, immunocytes may be collected from mammals immunized with antigens, investigated for the increase of the desired antibody level in serum (as above), and applied in cell fusion. Immunocytes for use in cell fusion preferably come from the spleen. Other preferred parent cells for fusion with the above immunogens include, but are not limited to, mammalian myeloma cells, and more preferably, myeloma cells that have acquired properties for selection of fusion cells by pharmaceutical agents.

The above immunocytes and myeloma cells can be fused using known methods, for example the methods of Milstein et al. (Galfre, G. and Milstein, C., (1981) Methods. Enzymol.: 73, 3-46.).

Hybridomas produced by cell fusion can be selected by culturing in a standard selective medium such as HAT medium (medium composed of hypoxanthine, aminopterin, and thymidine). Cell culture in HAT medium is usually continued for several days to several weeks, a period sufficient enough to kill all cells other than the desired hybridomas (unfused cells). Standard limiting dilutions may then be carried out, and hybridoma cells that produce the desired antibodies are screened and cloned.

Non-human animals can be immunized with antigens to prepare hybridomas in the above method. In addition, human lymphocytes from cells infected with EB virus or such, can be immunized in vitro using proteins, cells expressing proteins, or suspensions of the same. The immunized lymphocytes may then be fused with human-derived myeloma cells able to divide unlimitedly (U266 and so on), thus obtaining hybridomas that produce the desired human antibodies which can bind the protein (Unexamined Published Japanese Patent Application No. (JP-A) Sho 63-17688).

The obtained hybridomas may then be transplanted to mice abdominal cavities, and ascites are extracted. The obtained monoclonal antibodies can be purified using, for example, ammonium sulfate precipitation, protein A or protein G columns, DEAE ion exchange chromatography, or affinity columns coupled to the proteins of the present invention. The antibodies of the present invention can be used not only in purifying and detecting the proteins of the present invention, but also as candidates for agonists and antagonists of the proteins of the present invention. These antibodies can also be applied to antibody therapies for diseases related to the proteins of the present invention. When the obtained antibodies are administered to human bodies (antibody therapy), human antibodies or humanized antibodies are preferred due to their low immunogenicity.

For example, transgenic animals possessing a repertoire of human antibody genes can be immunized with antigens selected from proteins, protein-expressing cells, or suspensions of the same. Antibody-producing cells may then be recovered from the animals, fused with myeloma cells to yield hybridomas, and anti-protein human antibodies can be prepared from these hybridomas (see International Publication No. 92-03918, 94-02602, 94-25585, 96-33735, and 96-34096).

Alternatively, immunocytes such as immunized lymphocytes that produce antibodies, can be immortalized using cancer genes, and used to prepare monoclonal antibodies.

Monoclonal antibodies obtained in this way can be prepared using methods of genetic engineering (for example, see Borrebaeck, C. A. K. and Larrick, J. W., (1990) Therapeutic Monoclonal Antibodies, MacMillan Publishers, UK). For example, recombinant antibodies can be prepared by cloning DNAs that encode antibodies from immunocytes such as hybridomas or immunized lymphocytes that produce antibodies; then inserting these DNAs into appropriate vectors; and transforming these into host cells. Recombinant antibodies prepared as above are also contemplated in the present invention.

The antibodies can be modified by binding with a variety of molecules, for example polyethylene glycols (PEGs). Antibodies modified in this way can also be used in the present invention. Modified antibodies can be obtained by chemically modifying antibodies. These kinds of modification methods are conventional to those skilled in the art. The antibodies can also be modified by other proteins. Antibodies modified by protein molecules can be produced using genetic engineering. That is, target proteins can be expressed by fusing antibody genes with genes that code for modification proteins. For example, antibody effector function may be enhanced on binding with cytokines or chemokines. In fact, the enhancement of antibody effector function for proteins fused with IL-2, GM-CSF, and such has been confirmed (Penichet M L, et al., (2001) Human Antibodies, 10: 43-9.). IL-2, IL-12, GM-CSF, TNF, eosinophil chemotactic substance (RANTES) and so on can be included in cytokines or chemokines that enhance effector function.

Alternatively, antibodies of the present invention can be obtained as chimeric antibodies which contain a non-human antibody-derived variable region and a human antibody-derived constant region, or as humanized antibodies which contain a non-human antibody-derived complementarity determining region (CDR), a human antibody-derived framework region (FR), and a constant region. Such antibodies can be produced using known methods.

The standard techniques of molecular biology may be used to prepare DNA sequences coding for the chimeric and CDR-grafted products. Genes encoding the CDR of an antibody of interest can be prepared, for example, by using the polymerase chain reaction (PCR) to synthesize the variable region from RNA of antibody-producing cells (see, for example, Larrick et al., "Methods: a Companion to Methods in Enzymology", vol. 2: page 106 (1991); Courtenay-Luck, "Genetic Manipulation of Monoclonal Antibodies" in Monoclonal Antibodies: Production, Engineering and Clinical Application; Ritter et al. (eds.), page 166 (Cambridge University Press, 1995), and Ward et al., "Genetic Manipulation and Expression of Antibodies" in Monoclonal Antibodies: Principles and Applications; Birch et al. (eds.), page 137 (Wiley-Liss, Inc., 1995)). DNA sequences coding for the chimeric and CDR-grafted products may be synthesised completely or in part using oligonucleotide synthesis techniques. Site-directed mutagenesis and polymerase chain reaction techniques may be used as appropriate. For example, oligonucleotide directed synthesis as described by Jones et al., (1986) Nature.; 321:522-5 may be used. Also oligonucleotide directed mutagenesis of a pre-existing variable region as, for example, described by Verhoeyen et al., (1988) Science.; 239:1534-6 or Riechmann et al., (supra) may be used. Also enzymatic filling in of gapped oligonucleotides using T4 DNA polymerase as, for example, described by Queen et al., (1989) Proc Natl Acad Sci USA.; 86:10029-33; PCT Publication WO 90/07861 may be used.

Any suitable host cell/vector system may be used for expression of the DNA sequences coding for the CDR-grafted heavy and light chains. Bacterial, e.g., *E. coli*, and other microbial systems may be used, in particular for expression of antibody fragments such as FAb and (Fab')$_2$ fragments, and especially Fv fragments and single-chain antibody fragments, e.g., single-chain Fvs. Eucaryotic, e.g., mammalian, host cell expression systems may be used, in particular, for production of larger CDR-grafted antibody products, including complete antibody molecules. Suitable mammalian host cells include CHO cells and myeloma or hybridoma cell lines.

Antibodies obtained as above can be purified until uniform. For example, antibodies can be purified or separated according to general methods used for purifying and separating proteins. For example, antibodies can be separated and isolated using appropriately selected combinations of column chromatography, including but not limited to affinity chromatography, filtration, ultrafiltration, salt precipitation, dialysis, SDS polyacrylamide gel electrophoresis, isoelectric focusing, and so on (Antibodies: A Laboratory Manual, Harlow and David, Lane (edit.), Cold Spring Harbor Laboratory, 1988).

Protein A columns and Protein G columns can be used as affinity columns. Exemplary protein A columns in use include Hyper D, POROS, and Sepharose FF (Pharmacia).

Exemplary chromatography (excluding affinity chromatography) include ion exchange chromatography, hydrophobic chromatography, gel filtration, reverse phase chromatography, and adsorption chromatography ("Strategies for Protein Purification and Characterization: A Laboratory Course Manual" Daniel R. Marshak et al., (1996) Cold Spring Harbor Laboratory Press.). The chromatography can be performed according to the procedure of liquid phase chromatographies such as HPLC or FPLC.

For example, the antigen-binding activity of the antibodies of the present invention can be measured by using absorbance measurements, enzyme linked immunosorbent assays (ELISA), enzyme immunoassays (EIA), radioimmunoassays (RIA) and/or immunofluorescence methods. In ELISA, an antibody of the present invention is typically immobilized on a plate, a protein of the present invention is added to the plate, and then a sample containing the desired antibody such as the culture supernatant of cells that produce the antibody or purified antibody is added. A secondary antibody that recognizes the primary antibody and has been tagged with an enzyme such as alkaline phosphatase is then added, and the plate is incubated. After washing, an enzyme substrate such as p-nitrophenyl phosphate is added to the plate, absorbance is measured, and the antigen-binding activity of the samples is evaluated. Protein fragments (C-terminal or N-terminal fragments, and such) can be used in the same way as proteins. The binding activity of the antibodies of the present invention can be evaluated using BIAcore (Pharmacia).

In addition, by following the methods outlined in the Examples, antibody effector function can also be evaluated. For example, target EphA4-expressing cells can be incubated with effector cells in the presence of an antibody whose effector function is to be evaluated. If target cell destruction is detected, the antibody can be confirmed to possess effector function that induces ADCC. The level of observed target cell destruction, in the absence of either antibodies or effector cells, can be compared as a control with the level of effector function. Cells which clearly express EphA4 can be used as the target cells. Specifically, a variety of cell lines confirmed to express EphA4 in the Examples can be used. These cell lines can be obtained from cell banks. In addition, monoclonal antibodies which possess more powerful effector function can be selected.

In the present invention, anti-EphA4 antibodies can be administered to humans or other animals as pharmaceutical agents. In the present invention, animals other than humans to which the antibodies can be administered include, but are not limited to, mice, rats, guinea pigs, rabbits, chickens, cats, dogs, sheep, pigs, cows, monkeys, baboons, and chimpanzees. The antibodies can be directly administered to subjects, and in addition, can be formulated into dosage forms using known pharmaceutical formulation methods. For example, depending on requirements, they can be parenterally administered in an injectable form such as a sterile solution or suspension with water or other arbitrary pharmaceutically acceptable fluid. For example, this kind of compounds can be mixed with acceptable carriers or solvents, such as sterile water, physiological saline, vegetable oils, emulsifiers, suspension agents, surfactants, stabilizers, flavoring agents, excipients, solvents, preservatives, binding agents and the like, into a generally accepted unit dosage essential for use as a pharmaceutical agent.

Other isotonic solutions including physiological saline, glucose, and adjuvants (such as D-sorbitol, D-mannose, D-mannitol, and sodium chloride) can be used as the injectable aqueous solution. They can also be used with appropriate solubilizers such as alcohols, specifically ethanols and polyalcohols (for example, propylene glycols and polyethylene glycol), and non-ionic surfactants (for example Polysorbate 80™ or HCO-50).

Sesame oils or soybean oils can be used as an oleaginous solution, and benzyl benzoate or benzyl alcohols can be included as a solubilizer. Buffer solutions (phosphate buffers, sodium acetate buffers, or so on), analgesics (procaine hydrochloride or such), stabilizers (benzyl alcohol, phenols, or so on), and antioxidants can be included in the formulation. The prepared injections can be packaged into appropriate ampules.

In the present invention, the anti-EphA4 antibodies can be administered to patients, for example, intraarterially, intravenously, percutaneously, intranasally, transbronchially, locally, or intramuscularly. Intravascular (intravenous) administration by drip or injection is an example of a general method for systematic administration of antibodies to pancreatic cancer patients. Methods of locally concentrating antibody agents to the primary focus or metastatic focus in the lung include local injection using a bronchoscope (bronchoscopy) and local injection under CT guidance or with thoracoscopy. Methods of locally concentrating antibody agents to the primary focus or metastatic focus in the liver include local injection using a hepatic portal injection or arterial infusion. In addition, methods in which an intraarterial catheter is inserted near a vein that supplies nutrients to cancer cells to locally inject anti-cancer agents, such as antibody agents, are effective as local control therapies for metastatic focuses as well as primary focuses of pancreatic cancer.

Although dosage and administration methods vary according to patient body weight and age, and administration method, these parameters can be routinely determined by one skilled in the art. In addition, DNA encoding an antibody can be inserted into a vector for gene therapy, and the vector can be administered for therapy. Dosage and administration methods vary according to patient body weight, age, and condition; however, one skilled in the art can select these appropriately.

Anti-EphA4 antibodies can be administered to living bodies in an amount such that cytotoxicity based on effector function against EphA4-expressing cells can be confirmed. For example, although there is a certain amount of difference depending on symptoms, a typical dosage of anti-EphA4 antibody ranges from 0.1 mg to 250 mg/kg per day. Usually, the dosage for an adult (of weight 60 kg) is 5 mg to 17.5 g/day, preferably 5 mg to 10 g/day, and more preferably 100 mg to 3 g/day. The dosage schedule is from one to ten times over a two to ten day interval, and for example, progress is observed after a three to six times administration.

Although the antibodies of the present invention retain effector function, in some embodiments, cytotoxic agents can be linked to the antibodies using well known techniques. Cytotoxic agents are numerous and varied and include, but are not limited to, cytotoxic drugs or toxins or active fragments of such toxins. Suitable toxins and their corresponding fragments include, but are not limited to, diphtheria A chain, exotoxin A chain, ricin A chain, abrin A chain, curcin, crotin, phenomycin, enomycin, auristatin and the like. Cytotoxic agents also include radiochemicals made by conjugating radioisotopes to the antibodies of the invention or binding of a radionuclide to a chelating agent that has been covalently attached to the antibody. Methods for preparing such conjugates are well known in the art.

Alternatively, nucleic acids sequences encoding antibodies or functional derivatives thereof, can be administered to treat or prevent diseases associated with EphA4-expressing cells, such as pancreatic cancer, by way of gene therapy. Gene therapy refers to therapy performed by the administration to a subject of an expressed or expressible nucleic acid. In this embodiment of the invention, the nucleic acids produce their encoded antibody or antibody fragment that, in turn, mediates a prophylactic or therapeutic effect.

Any of the methods for gene therapy available in the art can be used according to the present invention. Exemplary methods are described below.

For general reviews of the methods of gene therapy, see Goldspiel et al., (1993) Clin. Pharm.; 12:488-505; Wu and Wu, (1991) Biotherapy.; 3:87-95; Tolstoshev, (1993) Ann Rev Pharmacol Toxicol.; 32:573-96; Mulligan, (1993) Science.; 260:926-32; Morgan and Anderson, (1993) Ann Rev Biochem.; 62:191-217; Clare Robinson Trends Biotechnol.; 11(5):155-215. Methods commonly known in the art of recombinant DNA technology which can be used are described in Ausubel et al. (eds.), Current Protocols in Molecular Biology, John Wiley & Sons, NY (1993); Kriegler, Gene Transfer and Expression, A Laboratory Manual, Stockton Press, NY (1990).

In a preferred aspect, a composition of the invention includes nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, (1989) Proc Natl Acad Sci USA.; 86:8932-5; Zijlstra et al., (1989) Nature.; 342:435-8). In specific embodiments, the expressed antibody molecule is a single chain antibody; alternatively, the nucleic acid sequences may include sequences encoding both the heavy and light chains, or fragments thereof, of the antibody.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In one embodiment, the nucleic acid sequence(s) can be directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, (1987) J Biol Chem.; 262:4429-32) (which can be used to target cell types specifically expressing the receptors), etc. In another embodiment, nucleic acid-ligand complexes can be formed in which the ligand includes a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180, WO 92/22635, WO92/20316, WO93/14188 or WO 93/20221). Alternatively, the nucleic acid can be introduced intracellularly and incorporated within host cell DNA for expression, by homologous recombination (Koller and Smithies, (1989) Proc Natl Acad Sci USA.; 86:8932-5; Zijlstra et al., (1989) Nature.; 342:435-8).

In one embodiment, viral vectors that contains nucleic acid sequences encoding an antibody of the invention or fragments thereof are used. For example, a retroviral vector can be used (see Miller et al., (1993) Methods Enzymol.; 217:581-99). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a subject. More detail about retroviral vectors can be found in Boesen et al., (1994) Biotherapy.; 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., (1994) J Clin Invest.; 93:644-51; Kiem et al., (1994) Blood.; 83:1467-73; Salmons and Gunzberg, (1993) Hum Gene Ther.; 4:129-41; Grossman and Wilson, (1993) Curr Opin Genet Dev.; 3:110-4.

Another example of a viral vector that can be used in gene therapy is the adenovirus. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, (1993) Curr Opin Genet Dev.; 3:499-503 present a review of adenovirus-based gene therapy. Bout et al., (1994) Hum Gene Ther.; 5:3-10 demonstrates the use of adenovirus vectors to transfer genes to the respiratory epithelia of rhesus monkeys. Other instances of the use of adenoviruses in gene therapy can be found in Rosenfeld et al., (1991) Science.; 252:431-4; Rosenfeld et al., (1992) Cell.; 68:143-55; Mastrangeli et al., (1993) J Clin Invest.; 91:225-34; PCT Publication WO94/12649; Wang et al., (1995) Gene Ther.; 2:775-83. In a preferred embodiment, adenovirus vectors are used.

Adeno-associated virus (AAV) has also been proposed for use in gene therapy (Walsh et al., (1993) Proc Soc Exp Biol Med.; 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells may then be delivered to a subject.

In this embodiment, the nucleic acid is introduced into a cell prior to administration in vivo of the resulting recombinant cell. Such introduction can be carried out by any method known in the art, including, but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, (1993) Methods Enzymol.; 217:599-618; Cotton et al., 1993, Methods Enzymol.; 217:618-44; Cline MJ. Pharmacol Ther. 1985; 29(1): 69-92.) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. In a preferred embodiment, the cell used for gene therapy is autologous to the subject.

In an embodiment in which recombinant cells are used in gene therapy, nucleic acid sequences encoding an antibody or fragment thereof can be introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, (1992) Cell.; 71:973-85; Rheinwald, (1980) Methods Cell Biol.; 21A:229-54; Pittelkow and Scott, (1986) Mayo Clin Proc.; 61:771-7).

In one preferred embodiment, the nucleic acid to be introduced for purposes of gene therapy includes an inducible promoter operably linked to the coding region, such that expression of the nucleic acid is controllable by controlling the presence or absence of the appropriate inducer of transcription.

In addition, the present invention provides immunogenic compositions for inducing antibodies possessing effector functions against EphA4-expressing cells, wherein the compositions contain as an active ingredient EphA4 or an immunologically active EphA4 fragment, or a DNA or cell which can express the same. Alternatively, the present invention relates to uses of EphA4 or an immunologically active EphA4 fragment, or a DNA or cell which can express the same in the production of immunogenic compositions for inducing antibodies possessing effector functions against EphA4-expressing cells.

The administration of anti-EphA4 antibodies damages cancer cells through the effector function of those antibodies. Thus, if EphA4 antibodies can be induced in vivo, therapeutic effects equivalent to the antibody administration can be achieved. When administering immunogenic compositions composed of antigens, target antibodies can be induced in vivo. The immunogenic compositions of the present invention thus are particularly useful in vaccine therapy against EphA4-expressing cells. Thus, the immunogenic compositions of the present invention are effective as, for example, vaccine compositions for pancreatic cancer therapies.

The immunogenic compositions of the present invention can include as an active ingredient EphA4 or an immunologically active EphA4 fragment. In the context of the present invention, an immunologically active EphA4 fragment refers to a fragment that can induce anti-EphA4 antibodies which recognize EphA4 and possess effector function. Below, EphA4 and the immunologically active EphA4 fragment are described as immunogenic proteins. Whether a given fragment induces target antibodies can be determined by actually immunizing an animal, and confirming the activity of the induced antibodies. Antibody induction and the confirmation of its activity can be carried out, for example, using methods described in Examples.

The immunogenic compositions of the present invention may contain pharmaceutically acceptable carriers as well as immunogenic proteins, the active ingredients. If necessary, the compositions can also be combined with an adjuvant. Killed tuberculosis bacteria, diphtheria toxoid, saponin and so on can be used as the adjuvant.

Alternatively, DNAs coding for the immunogenic proteins, or cells retaining those DNAs in an expressible state, can be used as the immunogenic compositions. Methods for using DNAs expressing the target antigen as immunogens, so-called DNA vaccines, are well known. DNA vaccines can be obtained by inserting a DNA encoding EphA4 or its fragment into an appropriate expression vector.

Retrovirus vectors, adenovirus vectors, adeno-associated virus vectors, Sendai virus vectors or such are examples of suitable vectors. In addition, DNAs in which a DNA encoding an immunogenic protein is functionally connected downstream of a promoter can be directly introduced into cells as naked DNA, and then expressed. Naked DNA can be encapsulated in ribosomes or viral envelope vectors and introduced into cells.

The EphA4 polypeptides and polynucleotides of the invention can also be used for the induction of an immune response in vivo, including production of antibodies and cytotoxic T lymphocytes (CTL) specific for EphA4 expressing cells. In such methods, CTL induction by a desired peptide can be achieved by presenting the peptide to a T cell via an antigen presenting cell (APC) either in vivo or ex vivo.

For example, patient blood cells e.g., peripheral blood mononuclear cells (PBMC) can be collected, transformed using a vector that can express the immunogenic proteins, and returned to the patient. Transformed bloods cells then produce the immunogenic proteins inside the body of the patient, and induce the target antibodies. Alternatively, PBMCs of the patient can be collected, contacted with the polypeptide ex vivo, and following the induction of APCs or CTLs, the cells may be administered to the subject. APCs or CTLs induced in vitro can be cloned prior to administration. By cloning and growing cells having high activity of damaging target cells, cellular immunotherapy can be performed more effectively. Furthermore, APCs and CTLs isolated in this manner may be used for cellular immunotherapy not only against individuals from whom the cells are derived, but also against similar types of tumors from other individuals.

Generally, when using a polypeptide for cellular immunotherapy, efficiency of the CTL-induction is known to be increased by combining a plurality of polypeptides having different structures and contacting them with APCs, particularly, dendritic cells. Therefore, when stimulating APCs with protein fragments, it is advantageous to use a mixture of multiple types of fragments.

The induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by those antibodies, the polypeptide is deemed to have the ability to induce anti-tumor immunity.

When DNAs encoding the immunogenic proteins, or cells transformed with the same are used as immunogenic compositions of the present invention, they can be combined with immunogenic proteins as well as carrier proteins that enhance their immunogenic properties.

As noted above, the present invention provides methods for inducing antibodies which possess effector function against EphA4-expressing cells, where the methods include the step of administering EphA4, an immunologically active EphA4 fragment, or DNA or cells that can express the same. The methods of the present invention induce antibodies that possess effector function that damages EphA4-expressing cells such as pancreatic cancers. As a result, therapeutic effects for pancreatic cancers and so on can be obtained.

Each day, 0.1 mg to 250 mg per kilogram of the immunogenic compositions of the present invention can be administered orally or parenterally. Parenteral administration includes subcutaneous injection and intravenous injection. The administrative dose for a single adult is usually 5 mg to 17.5 g/day, preferably 5 mg to 10 g/day, and more preferably 100 mg to 3 g/day.

The present invention also provides methods for treating or preventing cancers in a subject. In some embodiments, the method comprises the step of administering a pharmaceutically effective amount of an anti-EphA4 antibody, or immunologically active fragment thereof, wherein the antibody possesses antibody effector function.

All prior art references cited herein are incorporated by reference in their entirety.

BEST MODE FOR CARRYING OUT THE INVENTION

Figure 1:
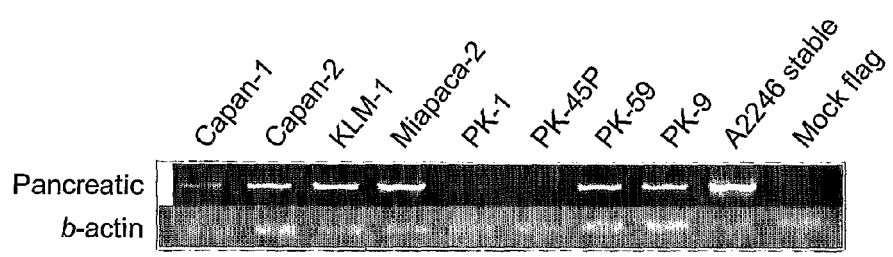
FIG. 1 is a photograph depicting the result of Semiquantitative RT-PCR analysis for the EphA4 gene in pancreatic cancer cell lines.

Hereinafter, the present invention is described in detail with reference to Examples. However, materials, methods and such described therein only illustrate aspects of the invention and in no way are intended to limit the scope of the present invention. As such, materials, methods and such similar or equivalent to those described therein may be used in the practice or testing of the present invention.

Cell Line:

Human colon or pancreatic cancer cell lines were propagated as a monolayer in an appropriate medium with 10% fetal bovine serum. The cell lines used in the experiment are shown in Table 1.

TABLE 1

| Pancreatic cancer Cell line | | |
|---|---|---|
| Cell line | Medium | Place obtained |
| PK-45P | RPMI + 10% FBS | TKG[*1]; TKG 0493 |
| PK-59 | RPMI + 10% FBS | TKG[*1]; TKG 0492 |
| KLM-1 | RPMI + 10% FBS | TKG[*1]; TKG 0490 |
| Capan-1 | RPMI + 10% FBS | ATCC; HTB-79 |
| Capan-2 | McCoy[*3] + 10% FBS | ATCC; HTB-80 |
| Miapaca-2 | E-MEM[*2] + 10% FBS | HSRRB; JCRB0070 |
| PK-1 | RPMI + 10% FBS | TKG[*1]; TKG 0239 |
| PK-9 | RPMI + 10% FBS | TKG[*1]; TKG 0240 |

[*1]Institute of Development, Aging and Cancer, Tohoku University
[*2]Eagle's Minimal Essential medium
[*3]McCoy's 5A medium Modified Furthermore, the following cell lines were used in ADCC assays using anti-EphA4 antibodies: Pancreatic carcinoma: MIAPaca-2.

Human Antibody:

Screening of the phage expression libraries using culture cells

For screening human scFV antibodies against EphA4, the phage library AIMS4 coding human scFV antibodies (WO01/62907) was used. The screening method is described in P2005-185281A.

For the first screening, first, MIAPaca-2 cells with high expression of EphA4 were cultured in 15 cm dishes, harvested with 2 mg/ml collagenase I (Gibco BRL)/cell dissociation buffer (Gibco BRL) and washed with cooled PBS. A solution of the human antibody phage library ($2 \times 10^{13}$ cfu) was mixed with $4 \times 10^7$ of the cells, BSA and NaN3/MEM. Final concentration was then adjusted to 1% BSA-0.1% NaN3/MEM in total volume of 1.6 ml, and the mixture was agitated gently for four hours at 4° C. After that, half of the reactive solution was dispensed into each of two tubes and centrifuged at 3000 rpm on the organic solvent (dibutyl phthalate: cyclohexane=9:1) for two minutes. After the supernatant was removed, the cells were resuspended in 0.7 ml of 1% BSA/MEM, and centrifuged on the equal volume of low polarity solvent. This step was repeated twice. The supernatant was removed, and the cells were then resuspended in 0.3 ml PBS, frozen with liquid nitrogen, and melted at 37° C.

These phages were allowed to infect 20 ml of *E. coli* DH12S (OD 0.5) for one hour, and the infected cells were transferred to 600 ml of 2×YTGA medium (2×YT, 200 µg/ml ampicillin sulfate, 1% glucose) and cultured overnight at 30° C. 10 ml of that was added to 200 ml of 2×YTA medium (2×YT, 200 µg/ml ampicillin sulfate) and cultured for 1.5 hour at 37° C. After additional incubation, $1 \times 10^{11}$ of helper phage KO7 was added and cultured for one hour at 37° C. again. After one hour of incubation as above, 800 ml of 2×YTGAK (2×YT, 200 µg/ml ampicillin sulfate, 0.05% glucose, 50 µg/ml kanamycin) was added and cultured for overnight at 30° C. This culture was centrifuged at 8000 rpm for ten minutes. The supernatant was mixed with 200 ml of PEG liquid (20% polyethyleneglycol 6000, 2.5 M NaCl) and centrifuged at 8000 rpm for 10 minutes to pellet the phage. This pellet was suspended in 10 ml of PBS and the part of suspension was used for examination of the number of *E. coli* infected by phage.

For the second screening, 0.8 ml of the reactive solution (1% BSA-0.1% NaN3/MEM), culture cells ($2 \times 10^7$) and 1st screened phage ($1 \times 10^{10}$) were used. A total volume of reactive solution was half of those used for 1st screening. 3rd screening was similar procedure to 2nd screening except that $2 \times 10^7$ of 293T cells transfected with EPHA4 and $1 \times 10^9$ of 2nd screened phage were used.

DNA Sequencing, Expression Check, and Cell ELISA of Antibody Clone

*E. coli* that was screened and diluted as described above was then cultivated on the nutrient agar with 100 µg/ml of ampicillin. The obtained colonies were isolated and incubated overnight at 30° C. with 2×YTGA medium. The DNA was obtained from the culture by PI-50 (Kurabo), and the DNA sequence was determined by dideoxy method.

Moreover, 0.05 ml of the culture was cultured with 1.2 ml of 2×YTAI (2×YT, 200 µg/ml ampicillin sulfate, 0.5 mM IPTG) at 30° C., and the supernatant was collected by centrifugation at 15000 rpm for 5 minutes.

The expression of the antibody was detected as a cp3 fusion protein. More specifically, the supernatant was reacted with Maxisorp™ (NUNC) for two hours at 37° C. and aspirated reacted solution. The plate with antibodies was blocked with 5% BSA for two hours at 37° C., removed blocking solution. Rabbit anti-cp3 antibody (MBL) diluted 1:2000 with 0.05% Tween/PBS was added to the plate and reacted at the room temperature for one hour, followed by washing with PBS. HRP tagged goat anti-rabbit IgG antibody (MBL) diluted 1:2000 with 0.05% Tween/PBS was added to the plate and reacted at the room temperature for one hour, followed by washing with PBS. 100 µl of OPD solution was added to the plate and reacted at the room temperature for 15 minutes, and the reaction was stopped by adding of 2M sulfuric acid ammonium. The fusion proteins were detected by measured the absorbance at 492 nm by SPECTRAmax 340PC (Molecular Devices).

Cell ELISA operation was as follows. First, the $1 \times 10^5$ of cells were cultured in 96 well plates overnight, the medium was replaced by 200 µl of 5% skimmed milk/PBS. After standing for three hours on the ice, the 100 µl of supernatant and 100 µl of 10% skimmed milk were mixed and remained on the ice overnight. After the five times washing with PBS storage on ice, the cells were reacted with 100 µl of 5 µg/ml mouse anti-cp3 monoclonal antibody, 5% skim milk/PBS for two hours at 4° C. After the five times washing with PBS storage on ice, the solution consisting of 25 µl of peroxidase tagged ENVISION+Polymer reagent and 75 µl of 15% skimmed milk/PBS was reacted to the cells for two hours at 4° C. After the five times washing with PBS storage on ice, the reaction was stopped by adding of 2M sulfuric acid ammonium, and the absorbance of the reaction mixture was measured at 492 nm by SPECTRAmax 340PC (Molecular Devices).

The human scFV antibodies positively reacted to antigen as confirmed by the flow cytometry were converted to complete IgG form in IFA.

These two clones had the following amino acid sequences.
65: SEQ ID NO: 9 (VH) and SEQ ID NO: 14 (VL)
336: SEQ ID NO: 19 (VH) and SEQ ID NO: 23 (VL)

These human scFV antibodies converted to complete IgG form in IFA. The following amino acid sequences were used as constant regions of heavy chain (CH) and light chain (CL).
CH(CH1, CH2, and CH3):

```
                                          (SEQ ID NO: 13)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LYKGFYPSDIAVEWESNGQPENNYKTTPPVLDSDGSFFLYSKLTVDKSRW

QQGNVFSCSVMHEAPHNHYTQKSLSLSPGK

CL:
                                          (SEQ ID NO: 18)
QPKAAPSVTLFPPSSEELQANKATLVCLISDFYPGAVTVAWKADSSPVKA

GVETTTPSKQSNNKYAASSYLSLTPEQWKSHRSYSCQVTHEGSTVEKTVA

PTECS
```

Semiquantitative RT-PCR for EphA4:

Total RNA was extracted from the cell lines using the Rneasy® Kit (QIAGEN). In addition, mRNA was purified from total RNA by Oligo (dT)-cellulose column (Amersham Biosciences) and synthesized to first-strand cDNA by reverse transcription (RT) using the SuperScript First-Strand Synthesis System (Invitrogen). It was prepared appropriate dilutions of each first-stranded cDNA for subsequent PCR amplification by monitoring GAPDH and β-actin as a quantitative control. The primer sequences utilized were as follows:

```
5'-GAAGGCGTGGTCACTAAATGTAA-3'   (SEQ.ID.NO.3)
and
5'-TTTAATTTCAGAGGGCGAAGAC-3'    (SEQ.ID.NO.4)
for EphA4, 5'-GTCAGTGGTGGACCTGACCT-3'      (SEQ.ID.NO.5)
and
5'-GGTTGAGCACAGGGTACTTTATT-3'   (SEQ.ID.NO.6)
for GAPDH, 5'-GAGGTGATAGCATTGCTTTCG-3'     (SEQ.ID.NO.7)
and
5'-CAAGTCAGTGTACAGGTAAGC-3'     (SEQ.ID.NO.8)
for β-actin.
```

All PCR reactions involved initial denaturation at 94° C. for 2 min and consisted of 94° C. for 30 s, 58° C. for 30 s, and 72° C. for 1 min by 21 cycles for GAPDH, 20 cycles for β-actin or 28-32 cycles for EphA4 on a GeneAmp PCR system 9700 (PE Applied Biosystems).

The over-expression of EphA4 was found in pancreatic cancer cell line Miapaca-2 (FIG. 1). In addition, to elucidate the efficacy of anti-EphA4 human antibody on various cancers, the expression of EphA4 was confirmed.

Flow Cytometry Analysis:

Cancer cells ($5 \times 10^6$) were incubated at 4° C. for 30 minutes with the purified polyclonal antibody (pAb), monoclonal antibodies (mAb), rabbit IgG (the control for pAb) or mouse IgG (the control for mAb). Cells were washed with phosphate buffer solution (PBS) and then incubated at 4° C. for 30 minutes in FITC-labeled Alexa Fluor 488. The cells were again washed in PBS, and analyzed on a flow cytometer (FACSCalibur®, Becton Dickinson) and then analyzed by BD CellQuest™ Pro software (Becton Dickinson). Mean fluorescence intensity (MFI) was defined as a ratio of the flow cytometric intensity (intensity by each protein specific antibody/intensity by rabbit IgG).

Using EphA4 over-expressing cells, the binding ratios of anti-EphA4 antibodies on the cell surface were investigated. As a result, a higher proportion of anti-EphA4 human antibodies 65 and 336 bound to MIAPaca-2 cells (MFI: 12.64 and 15.54, respectively) than did human IgG (the control).

ADCC Assays:

Target cells were exposed with 0.8 μM of calcein acetoxymethyl ester (Calcein-AM, DOJINDO) at 37° C. for 30 minutes. Calcein-AM becomes fluorescent after the cleavage of calcein-AM by cellular esterases that produce a fluorescent derivate calcein. Target cancer cells were washed two times before being added to the assay, and cells were then plated on 96-well U-bottom plates ($4 \times 10^3$ cells/well). Human peripheral blood mononuclear cells (PMBC) were harvested from a healthy person, separated using Ficoll-Paque (Amersham Biosciences) density gradient centrifugation, and then used as effector cells. Target cancer cells (T) and effector cells (E) were co-incubated in 250 μl of AIM-V medium in 96-well plates E:T ratios 100:1 with anti-EphA4 human antibody at various concentrations (0, 0.01, 0.1, 1, 10, 100 μg/well) or control antibody Herceptin (Roche). This incubation was carried out in triplicate, in 250 μL of AIM-V medium (Life Technologies, Inc), at 37° C. for six hours. Control assays included the incubation of target cells with only anti-EphA4 human antibody or effector cells. Herceptin was used as a control in some experiments.

The ADCC effects of anti-EphA4 human antibody (65 and 336) for these cells were evaluated based on the fluorescent images of viable cells were rapidly acquired using the IN Cell Analyzer 1000 (Amersham Bioscience). These images were numerically converted as viable cell count (cell area for target cells) by counting the fluorescent object or vesicle using Developer tool ver.5.21 software (Amersham Bioscience).

Figure 2:
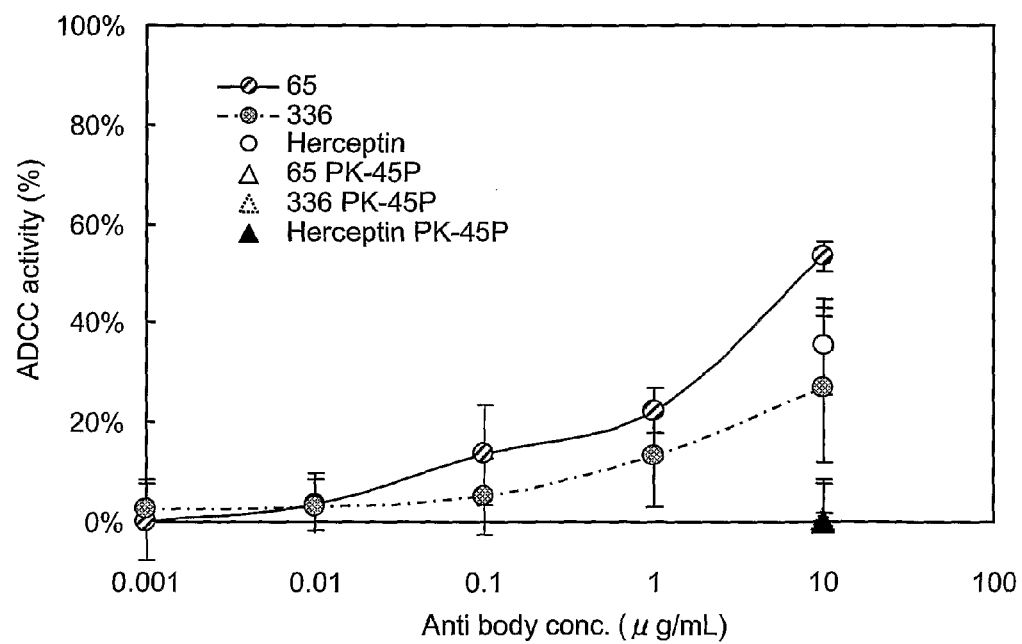
FIG. 2 depicts the results of an ADCC assay using Herceptin and anti-EphA4 human antibody 65 and 336 against EphA4-over- and -low-expressing pancreatic cancer cell line, MIAPaca-2 and PK-45P.

Herceptin was used as a control in several experiments. Direct cell damage of MIAPaca-2 cells by 65 and 336 anti-EphA4 human antibodies itself was not observed. However, 65 and 336 anti-EphA4 human antibodies induced ADCC in MIAPaca-2 cells that over-expressed EphA4 (FIG. 2), while no effect against PK-45P cells with EphA4 low-expression (FIG. 2).

INDUSTRIAL APPLICABILITY

The present invention is based, at least in part, on the discovery that EphA4-expressing cells can be damaged by antibody cytotoxicity. EphA4 was identified by the present inventors as a gene strongly expressed in pancreatic cancers. Thus, treatment of disease associated with EphA4-expressing cells, for example, pancreatic cancer is conveniently carried out using antibodies that bind to EphA4. Results actually confined by the present inventors show cytotoxicity due to the effect of ADCC in pancreatic cancer cell lines, in the presence of EphA4 antibodies.

While the invention has been described in detail and with reference to specific embodiments thereof, it will be apparent to those skilled in the art that various changes and modifications can be made therein without departing from the spirit and scope of the invention, the metes and bounds of which are set by the appended claims.

The invention claimed is:

1. A method for treating a pancreatic cancer expressing EphA4 in a subject comprising the step of administering to said subject an amount of an antibody that specifically binds to Eph4A, wherein the antibody comprises a heavy chain variable domain (VH) comprising the complementarity determining region (CDR) amino acid sequences of SEQ ID NO: 10(VH-CDR1), SEQ ID NO:11 (VH-CDR2) and SEQ ID NO:12 (VH-CDR3) separated by antibody framework amino acid sequences and a light chain variable domain (VL) comprising the CDR amino acid sequences of SEQ ID NO:15 (VL-CDR1), SEQ ID NO:16(VL-CDR2) and SEQ ID NO:17 (VL-CDR3) separated by antibody framework amino acid sequences, wherein the antibody causes antibody-dependent cytotoxicity, complement-dependent cytotoxicity or both and wherein the amount administered is effective to treat said pancreatic cancer expressing EphA4.

2. The method of claim 1, wherein the VH comprises the amino acid sequence of SEQ ID NO: 27 and the VL comprises the amino acid sequence of SEQ ID NO: 28.

3. A method for treating a pancreatic cancer expressing EphA4 in a subject comprising the step of administering to said subject an amount of an antibody that specifically binds to Eph4A, wherein the antibody comprises a heavy chain variable domain (VH) comprising the complementarity determining region (CDR) amino acid sequences of SEQ ID NO: 20 (VH-CDR1), SEQ ID NO:21 (VH-CDR2) and SEQ ID NO:22(VH-CDR3) separated by antibody framework amino acid sequences and a light chain variable domain (VL) comprising the CDR amino acid sequences of SEQ ID NO:24 (VL-CDR1), SEQ ID NO:25 (VL-CDR2) and SEQ ID NO:26 (VL-CDR3) separated by antibody framework amino acid sequences, wherein the antibody causes antibody-dependent cytotoxicity, complement-dependent cytotoxicity or both and wherein the amount administered is effective to treat said pancreatic cancer expressing EphA4.

4. The method of claim 3, wherein the VH comprises the amino acid sequence of SEQ ID NO: 29 and the VL comprises the amino acid sequence of SEQ ID NO: 30.

5. A method for treating a pancreatic cancer expressing EphA4 in a subject comprising the step of administering to said subject an amount of an antibody that specifically binds to Eph4A, or antigen-binding fragment thereof, wherein the antibody or antigen-binding fragment thereof comprises a heavy chain variable domain (VH) comprising the complementarity determining region (CDR) amino acid sequences of SEQ ID NO: 10 (VH-CDR1), SEQ ID NO:11 (VH-CDR2) and SEQ ID NO:12 (VH-CDR3) separated by antibody framework amino acid sequences and a light chain variable domain (VL) comprising the CDR amino acid sequences of SEQ ID NO:15 (VL-CDR1), SEQ ID NO:16 (VL-CDR2) and SEQ ID NO:17 (VL-CDR3) separated by antibody framework amino acid sequences, wherein the antibody or antigen-binding fragment thereof is conjugated to a cytotoxic agent and wherein the amount administered is effective to treat said pancreatic cancer expressing EphA4.

6. The method of claim 5, wherein the VH comprises the amino acid sequence of SEQ ID NO: 27 and the VL comprises the amino acid sequence of SEQ ID NO: 28.

7. A method for treating a pancreatic cancer expressing EphA4 in a subject comprising the step of administering to said subject an amount of an antibody that specifically binds to Eph4A, or antigen-binding fragment thereof, wherein the antibody or antigen-binding fragment thereof comprises a heavy chain variable domain (VH) comprising the complementarity determining region (CDR) amino acid sequences of SEQ ID NO: 20 (VH-CDR1), SEQ ID NO:21 (VH-CDR2) and SEQ ID NO:22 (VH-CDR3) separated by antibody framework amino acid sequences and a light chain variable domain (VL) comprising the CDR amino acid sequences of SEQ ID NO:24 (VL-CDR1), SEQ ID NO:25 (VL-CDR2) and SEQ ID NO:26 (VL-CDR3) separated by antibody framework amino acid sequences, wherein the antibody or antigen-binding fragment thereof is conjugated to a cytotoxic agent and wherein the amount administered is effective to treat said pancreatic cancer expressing EphA4.

8. The method of claim 7, wherein the VH comprises the amino acid sequence of SEQ ID NO: 29 and the VL comprises the amino acid sequence of SEQ ID NO: 30.

* * * * *